US011723989B2

United States Patent
Wilson et al.

(10) Patent No.: US 11,723,989 B2
(45) Date of Patent: Aug. 15, 2023

(54) GENE THERAPY FOR MUCOPOLYSACCHARIDOSIS IIIB

(71) Applicant: The Trustees of the University of Pennsylvania, Philadelphia, PA (US)

(72) Inventors: James M. Wilson, Philadelphia, PA (US); Christian Hinderer, New Orleans, LA (US); Juliette Hordeaux, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 372 days.

(21) Appl. No.: 16/768,547

(22) PCT Filed: Nov. 29, 2018

(86) PCT No.: PCT/US2018/063166
§ 371 (c)(1),
(2) Date: May 29, 2020

(87) PCT Pub. No.: WO2019/108856
PCT Pub. Date: Jun. 6, 2019

(65) Prior Publication Data
US 2020/0289675 A1    Sep. 17, 2020

Related U.S. Application Data

(60) Provisional application No. 62/593,090, filed on Nov. 30, 2017.

(51) Int. Cl.
*A61K 35/76* (2015.01)
*C12N 7/00* (2006.01)
*A61K 48/00* (2006.01)
*C12N 15/86* (2006.01)

(52) U.S. Cl.
CPC .......... *A61K 48/0075* (2013.01); *A61K 35/76* (2013.01); *C12N 7/00* (2013.01); *C12N 15/86* (2013.01); *C12N 2750/14121* (2013.01); *C12N 2750/14132* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,596,535 B1 | 7/2003 | Carter | |
| 7,125,717 B2 | 10/2006 | Carter | |
| 7,282,199 B2 | 10/2007 | Gao et al. | |
| 7,456,683 B2 | 11/2008 | Takano et al. | |
| 7,588,772 B2 | 9/2009 | Kay et al. | |
| 7,790,449 B2 | 9/2010 | Gao et al. | |
| 7,906,111 B2 | 3/2011 | Wilson et al. | |
| 8,927,514 B2 | 1/2015 | Chatterjee et al. | |
| 9,102,949 B2 | 8/2015 | Gao et al. | |
| 9,585,971 B2 | 3/2017 | Deverman et al. | |
| 9,623,120 B2 | 4/2017 | Chatterjee et al. | |
| 2007/0036760 A1 | 2/2007 | Wilson et al. | |
| 2009/0197338 A1 | 8/2009 | Vandenberghe et al. | |
| 2013/0039888 A1 | 2/2013 | McCarty et al. | |
| 2013/0045186 A1 | 2/2013 | Gao et al. | |
| 2015/0079038 A1 | 3/2015 | Deverman et al. | |
| 2015/0349911 A1 | 12/2015 | Ostubo | |
| 2017/0088859 A1 | 3/2017 | Bosch et al. | |

FOREIGN PATENT DOCUMENTS

| | | |
|---|---|---|
| EP | 1310571 | 2/2006 |
| WO | WO 96/09378 | 3/1996 |
| WO | WO 2003/042397 | 5/2003 |
| WO | WO 2005/033321 | 4/2005 |
| WO | WO 2006/110689 | 10/2006 |
| WO | WO 2010/053572 | 5/2010 |
| WO | WO 2011/126808 B2 | 10/2011 |
| WO | WO 2012/170930 | 12/2012 |
| WO | WO 2013/182683 | 12/2013 |
| WO | WO 2014/151341 | 9/2014 |
| WO | WO 2015/173308 | 11/2015 |
| WO | WO 2015/173308 A1 | 11/2015 |
| WO | WO 2016/049230 A1 | 3/2016 |
| WO | WO 2016/187017 A1 | 11/2016 |
| WO | WO 2017/100682 A1 | 6/2017 |
| WO | WO 2017/132675 A1 | 8/2017 |
| WO | WO 2017/136500 | 8/2017 |
| WO | WO 2017/136533 | 8/2017 |

(Continued)

OTHER PUBLICATIONS

Burkholder et al., Health Evaluation of Experimental Laboratory Mice, Current Protocols in Mouse Biology, vol. 2:145-165, Jun. 2012.

Guyenet et al., A simple composite phenotype scoring system for evaluating mouse models of cerebellar ataxia, Journal of Visualized Experiments: JoVE, (39):1787, May 2010.

Tumpey et al., Absence of macrophage inflammatory protein-1alpha prevents the development of blinding herpes stromal keratitis, Journal of Virology, vol. 72(5):3705-10, May 1998.

Lock et al., Absolute Determination of Single-Stranded and Self-Complementary Adeno-Associated Viral Vector Genome Titers by Droplet Digital PCR. Human Gene Therapy Methods, vol. 25(2):115-125, Apr. 2014.

(Continued)

*Primary Examiner* — Benjamin P Blumel
(74) *Attorney, Agent, or Firm* — Howson & Howson; Cathy A. Kodroff

(57) ABSTRACT

Provided herein is a recombinant AAV (rAAV) comprising an AAV capsid and a vector genome packaged therein, wherein the vector genome comprises an AAV 5' inverted terminal repeat (ITR), an engineered nucleic acid sequence encoding a functional human N-acetyl-alpha-glucosaminidase (hNAGLU), a regulatory sequence which direct expression of hNAGLU in a target cell, and an AAV 3' ITR. Also provided is a pharmaceutical composition comprising a rAAV as described herein in a formulation buffer, and a method of treating a human subject diagnosed with MPS IIIB.

28 Claims, 5 Drawing Sheets

Specification includes a Sequence Listing.

(56) References Cited

FOREIGN PATENT DOCUMENTS

| WO | WO 2017/160360 | 9/2017 |
|---|---|---|
| WO | WO 2018/160582 | 9/2018 |

OTHER PUBLICATIONS

Lock et al., Rapid, Simple, and Versatile Manufacturing of Recombinant Adeno-Associated Viral Vectors at Scale, Human Gene Therapy, 21(10):1259-1271, Oct. 2010.

Zhao et al., Purification and characterization of recombinant human alpha-N-acetylglucosaminidase secreted by Chinese hamster ovary cells, Protein Expression and Purification, vol. 19(1):202-211, Jun. 2000.

Ficko-Blean et al., Structural and mechanistic insight into the basis of mucopolysaccharidosis IIIB, PNAS, vol. 105(18):6560-6565, May 2008.

Boado et al., Insulin Receptor Antibodyalpha-N-Acetylglucosaminidase Fusion Protein Penetrates the Primate Blood-Brain Barrier and Reduces Glycosoaminoglycans in Sanfilippo Type B Fibroblasts, Molecular Pharmaceutics, vol. 13(4): 1385-92, Feb. 2016.

Kan et al., Insulin-like growth factor II peptide fusion enables uptake and lysosomal delivery of alpha-N-acetylglucosaminidase to mucopolysaccharidosis type IIIB fibroblasts, Biochemical Journal, vol. 458(2):281-9, Feb. 2014.

Ruijter et al., Genistein in Sanfilippo disease: a randomized controlled crossover trial, Annals of Neurology, vol. 71(1):110-20, Jan. 2012.

Coutinho et al., Less is More: Substrate Reduction Therapy for Lysosomal Storage Disorders, International Journal of Molecular Sciences, vol. 17:1065, Jul. 2016.

Aoyagi-Scharber et al., Clearance of Heparan Sulfate and Attenuation of CNS Pathology by Intracerebroventricular BMN 250 in Sanfilippo Type B Mice, Molecular Therapy—Methods & Clinical Development, vol. 6:43-53, Sep. 2017.

Piotrowska et al., Genistin-rich soy isoflavone extract in substrate reduction therapy for Sanfilippo syndrome: An open-label, pilot study in 10 pediatric patients, Current Therapeutic Research, Clinical and Experimental, vol. 69(2):166-79, Apr. 2008.

Piotrowska et al., Two-year follow-up of Sanfilippo Disease patients treated with a genistein-rich isoflavone extract: assessment of effects on cognitive functions and general status of patients, Medical Sci Monit., vol. 17(4):CR196-202, Apr. 2011.

Delgadillo et al., Genistein supplementation in patients affected by Sanfilippo disease, Journal of Inherited Metabolic Disease, vol. 34(5):1039-44, Oct. 2011.

Garbuzova-Davis, et al., Intravenous administration of human umbilical cord blood cells in an animal model of MPS III B, The Journal of Comparative Neurology, vol. 515(1):93-101, Jul. 2009.

Garbuzova-Davis et al., Transplantation of human umbilical cord blood cells benefits an animal model of Sanfilippo syndrome type B, Stem Cells and Development, vol. 14(4):384-394, Sep. 2005.

Vellodi et al., Bone marrow transplantation for Sanfilippo disease type B, Journal of Inherited Metabolic Diseases, vol. 15(6):911-8, 1992.

Walf et al., The use of the elevated plus maze as an assay of anxiety-related behavior in rodents, Nature Protocols, vol. 2(2):322-8, 2007.

Tatem et al., Behavioral and locomotor measurements using an open field activity monitoring system for skeletal muscle diseases, Journal of Visualized Experiments, JoVE, (91):51785, Sep. 2014.

Hinderer et al., Widespread gene transfer in the central nervous system of cynomolgus macaques following delivery of AAV9 into the cisterna magna, Molecular Therapeitucs Methods Clin Dev., vol. 1:14051, Dec. 2014.

Rose et al., Structural proteins of adenovirus-associated viruses, Journal of Virology, vol. 8(5):766-770, Nov. 1971.

Buller et al., Characterization of adenovirus-associated virus-induced polypeptides in KB cells, Journal of Virology, vol. 25(1):331-338, Jan. 1978.

Rayaprolu et al., Comparative Analysis of Adeno-Associated Virus Capsid Stability and Dynamics, Journal of Virology, vol. 87(24):13150-13160, Dec. 2013.

Wobus et al., Monoclonal antibodies against the adeno-associated virus type 2 (AAV-2) capsid: epitope mapping and identification of capsid domains involved in AAV-2-cell interaction and neutralization of AAV-2 infection, Journal of Virology, vol. 74(19):9281-93, Oct. 2000.

Sommer et al., Quantification of adeno-associated virus particles and empty capsids by optical density measurement, Molecular Therapy, vol. 7(1):122-8, Jan. 2003.

Grimm et al., Titration of AAV-2 particles via a novel capsid ELISA: packaging of genomes can limit production of recombinant AAV-2, Gene Therapy, vol. 6:1322-1330, Aug. 1999.

Kotin, R., Large scale recombinant adeno-associated virus production. Human Molecular Genetics, vol. 20(R1):R2-6, Apr. 2011.

Galibert et al., Latest developments in the large-scale production of adeno-associated virus vectors in insect cells toward the treatment of neuromuscular diseases, Journal of Invertebrate Pathology, vol. 107 Suppl:S80-93, Jul. 2011.

Li et al., Production and characterization of novel recombinant adeno-associated virus replicative-form genomes: a eukaryotic source of DNA for gene transfer, PLoS One, vol. 8(8):e69879, Aug. 2013.

Mtetzsch et al., OneBac 2.0: Sf9 Cell Lines for Production of AAV1, AAV2, and AAV8 Vectors with Minimal Encapsidation of Foreign DNA. Human Gene Therapy Methods, vol. 28(1):15-22, Feb. 2017.

French et al., What is a conservative substitution? Journal of Molecular Evolution, vol. 19(2):171-175, 1983.

Yampolsky et al. The Exchangeability of Amino Acids in Proteins, Genetics, vol. 170(4): 1459-1472, Aug. 2005.

Kan et al., Delivery of an enzyme-IGFII fusion protein to the mouse brain is therapeutic for mucopolysaccharidosis type IIIB. PNAS, vol. 111(41):14870-5, Oct. 2014.

Green and Sambrook, Molecular Cloning: A Laboratory Manual, Cold 20 Spring Harbor Press, Cold Spring Harbor, NY (2012).

Thompson et al., A comprehensive comparison of multiple sequence alignments, Nucleic Acids Research, vol. 27(13):2682-2690, 1999.

Kim et al., Use of the human elongation factor 1 alpha promoter as a versatile and efficient expression system, Gene, vol. 91(2):217-23, Jul. 1990.

Kügler et al., Human synapsin 1 gene promoter confers highly neuron-specific long-term transgene expression from an adenoviral vector in the adult rat brain depending on the transduced area, Gene Therapy, vol. 10(4):337-47, Feb. 2003.

Kim et al., Involvement of cholesterol-rich lipid rafts in interleukin-6-induced neuroendocrine differentiation of LNCaP prostate cancer cells, Endocrinology, vol. 145(2):613-9, Feb. 2004.

Rashnonejad et al., Large-Scale Production of Adeno-Associated Viral Vector Serotype-9 Carrying the Human Survival Motor Neuron Gene, Molecular Biotechnology, vol. 58(1):30-6, Jan. 2016.

Miyatake et al., Transcriptional targeting of herpes simplex virus for cell-specific replication, Journal of Virology, vol. 71(7):5124-32, Jul. 1997.

Sandig et al., HBV-derived promoters direct liver-specific expression of an adenovirally transduced LDL receptor gene, Gene Therapy, vol. 3(11):1002-9, Nov. 1996.

Arbu Thnot et al., In vitro and in vivo hepatoma cell-specific expression of a gene transferred with an adenoviral vector, Human Gene Therapy, vol. 7(13):1503-14, Aug. 1996.

Andersen et al., Herpesvirus-mediated gene delivery into the rat brain: specificity and efficiency of the neuron-specific enolase promoter, Cellular and Molecular Neurobiology, vol. 13:503-15, Oct. 1993.

Piccioli et al., Neuroantibodies: molecular cloning of a monoclonal antibody against substance P for expression in the central nervous system, PNAS, vol. 88(13):5611-5, Jul. 1991.

Piccioli et al., Neuroantibodies: ectopic expression of a recombinant antisubstance P antibody in the central nervous system of transgenic mice, Neuron, vol. 15(2):373-84, Aug. 1995.

Su et al., In vitro and in vivo mRNA delivery using lipid-enveloped pH-responsive polymer nanoparticles, Molecular Pharmaceutics, vol. 8(3):774-787, Jun. 2011.

GenBank Accession No. AY530579.1, dated Jun. 24, 2004.

(56) References Cited

OTHER PUBLICATIONS

GenBank Accession No. AAS99264, dated Jun. 24, 2004.

Gao et al., Adeno-associated viruses undergo substantial evolution in primates during natural infections, PNAS, vol. 100(10):6081-6086, May 2003.

McCarty et al., Self-complementary recombinant adeno-associated virus (scAAV) vectors promote efficient transduction independently of DNA synthesis, Gene Therapy, vol. 8(16):1248-1254, Aug. 2001.

Aucoin et al., Production of adeno-associated viral vectors in insect cells using triple infection: optimization of baculovirus concentration ratios, Biotechnology and Bioengineering, vol. 20;95(6):1081-92, Dec. 2006.

Thakur, S., Production of Recombinant Adeno-associated viral vectors in yeast, Thesis presented to the Graduate School of the University of Florida, 2012.

Kondratov et al., Direct Head-to-Head Evaluation of Recombinant Adeno-associated Viral Vectors Manufactured in Human versus Insect Cells, Molecular Therapy, vol. 25(12):2661-2675, Dec. 2017.

International Preliminary Report on Patentability in PCT/US2018/063166, dated Jun. 2, 2021.

Office Action issued in correponding Chilean Patent Application No. 2020-01428, dated Aug. 30, 2021.

Extended European Search Report issued in European Patent Application No. 18882454.4, dated Oct. 27, 2021.

Office Action issued in corresponding Eurasian Patent Application No. 2020-91352, dated Aug. 11, 2022, with translation of Official Action as provided by agent.

Office Action issued in corresponding Japanese Patent Application No. 2020-529431, dated Oct. 26, 2022, with translation of Notice of Reasons for Rejection as provided by agent.

Office Action issued in corresponding Eurasian Patent Application No. 2020-91352, dated Feb. 27, 2023, with translation of Official Action as provided by agent.

| | Fur Quality |
|---|---|
| 0 | Shiny coat, smooth fur, well groomed, clean coat |
| 1 | Not well groomed, slightly oily or rough coat |
| 2 | Rough Hair coat - haircoat is oily, dirty, stands on end |
| 3 | Very rough hair coat, dehydration |
| | Gait / Mobility |
| 0 | Active, energetic |
| 1 | Able to run, but sluggish |
| 2 | Reluctant to move, but will respond to prodding |
| 3 | Moves only when manually prodded & minimally |
| | Tremor |
| 0 | No sign of tremor |
| 1 | Very slight, impermanent |
| 2 | Mild, visible when compared to WT |
| 3 | Moderate, evident without comparison |
| 4 | Severe, impacts mobility |
| | Clasping |
| 0 | Legs splay out when lifted |
| 1 | 1 leg pulls in, not permanent |
| 2 | 1 leg permanently OR both legs impermanently pulled inward |
| 3 | 1 permanent and 1 impermanent leg pulled inward |
| 4 | Both legs pull in, permanent |
| | Posture |
| 0 | Normal, flat back |
| 1 | Transitory hunching, evident only when resting or lifted by tail only |
| 2 | Rests upright with back hunched, back stays hunched when moving |
| 3 | Almost always hunched |
| | Corneal Opacity |
| 0 | Clear Cornea |
| 1 | Slight Corneal Haze |
| 2 | Moderate Corneal Opacity |
| 3 | Severe Corneal Opacity - Iris visible |
| 4 | Severe Corneal Opacity - Iris not visible |

FIG. 5

GENE THERAPY FOR MUCOPOLYSACCHARIDOSIS IIIB

CROSS-REFERENCE TO RELATED APPLICATIONS

This is a National Stage Entry under 35 U.S.C. 371 of International Patent Application No. PCT/US2018/063166, filed Nov. 29, 2018, which claims priority to U.S. Provisional Patent Application No. 62/593,090, filed Nov. 30, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "18-8482PCT_ST25.txt".

BACKGROUND OF THE INVENTION

Mucopolysaccharidosis type IIIB (MPS IIIB, or Sanfilippo syndrome type B, Sanfilippo type B disease), is an autosomal recessive inherited disorder caused by the deficiency of the enzyme N-acetyl-alpha-D-glucosaminidase (NAGLU) involved in the lysosomal catabolism of the glycosaminoglycans (GAG) heparan sulfate. This deficiency leads to the intracellular accumulation of undegraded heparan sulfate as well as gangliosides GM2 and GM3 in the central nervous system causing neuronal dysfunction and neuroinflammation.

MPS IIIB is a neurodegenerative disorder characterized by an initial symptom free period followed by progressive intellectual decline, finally resulting in severe dementia. Severe behavioral problems are a predominant symptom in most patients, characterized mainly by extremely hyperactive behavior. Other symptoms include sleeping problems, recurrent diarrhea, frequent ear, nose and throat infections, hearing and visual impairment and epilepsy. Patients usually die at the end of the second or the beginning of the third decade of life, although longer survival has been reported in patients with an attenuated form of MPS IIIB.

There is no specific treatment for MPS IIIB. Clinical management of patients with MPS IIIB currently still consists mainly of supportive care, aimed at ameliorating symptoms and prevention of complications. Medications are used to relieve symptoms (such as anticonvulsants for seizures) and improve quality of life. Hematopoietic stem cell transplantation, such as bone marrow transplantation or umbilical cord blood transplantation, does not seem to ameliorate neuropsychological deterioration significantly. Enzyme replacement therapies (ERT) for MPS IIIB via intravenous administration and intracerebroventricular infusion shows elevated enzyme activity of NAGLU in murine models and are currently under investigation in clinical trials on MPS MB patients. Still, ERT requires multiple administrations, significantly impacts patient quality of life, and is at a high expense. See, e.g., Aoyagi-Scharber M et al, Clearance of Heparan Sulfate and Attenuation of CNS Pathology by Intracerebroventricular BMN 250 in Sanfilippo Type B Mice, Mol Ther Methods Clin Dev. 2017 Jun. 6; 6:43-53. doi: 10.1016/j.omtm.2017.05.009. eCollection 2017 Sep. 15; and WO2017132675A1.

A need in the art exists for compositions and methods for efficient treatment of MPS IIIB.

SUMMARY OF THE INVENTION

In one aspect, provided herein is a vector comprising an engineered nucleic acid sequence encoding a functional human N-acetyl-alpha-glucosaminidase (hNAGLU) and a regulatory sequence which direct expression thereof in a target cell. In one embodiment, the hNAGLU coding sequence is at least 95% identical to SEQ ID NO: 1. In a further embodiment, the hNAGLU coding sequence is SEQ ID NO: 1.

In another aspect, provided is a recombinant AAV (rAAV) comprising an AAV capsid and a vector genome packaged therein, wherein the vector genome comprises an AAV 5' inverted terminal repeat (ITR), an engineered nucleic acid sequence encoding a functional hNAGLU, a regulatory sequence which direct expression of hNAGLU in a target cell, and an AAV 3' ITR. In one embodiment, the hNAGLU coding sequence is at least 95% identical to SEQ ID NO: 1. In a further embodiment, the hNAGLU coding sequence is SEQ ID NO: 1. In yet a further embodiment, the AAV vector genome comprises the sequence of SEQ ID NO: 4 (AAV.CB7.CI.hNAGLUco.rBG). In some embodiments, the AAV capsid is an AAV9 capsid. In one embodiment, the rAAV (AAV9.CB7.CI.hNAGLUco.rBG) comprises an AAV9 capsid and a vector genome comprising the sequence of SEQ ID NO: 4.

In yet another aspect, a pharmaceutical composition comprising a rAAV in a formulation buffer is provided, wherein the rAAV comprises an AAV capsid and a vector genome packaged therein, wherein the vector genome comprises an AAV 5' inverted terminal repeat (ITR), an engineered nucleic acid sequence encoding a functional hNAGLU, a regulatory sequence which direct expression of hNAGLU in a target cell, and an AAV 3' ITR.

In a further aspect, a method of treating a human subject diagnosed with MPS IIIB is provided. The method comprises administering to a subject in need a suspension of a rAAV as described herein in a formulation buffer.

Further provided are an engineered nucleic acid sequence comprising an engineered sequence of SEQ ID NO: 1 or a sequence 95% identical thereto and an expression cassette comprising an engineered nucleic acid sequence encoding a functional hNAGLU, and a regulatory sequence which direct expression thereof. In one embodiment, the hNAGLU coding sequence is at least 95% identical to SEQ ID NO: 1.

Other aspects and advantages of the invention will be readily apparent from the following detailed description of the invention.

BRIEF DESCRIPTION OF THE DRAWINGS

FIG. 5 provides a grading scale used to assess the clinical health of mice used in studies to determine long-term effects of AAV9.CB7.CI.hNAHLU.rBG treatment.

DETAILED DESCRIPTION OF THE INVENTION

Figure 1:
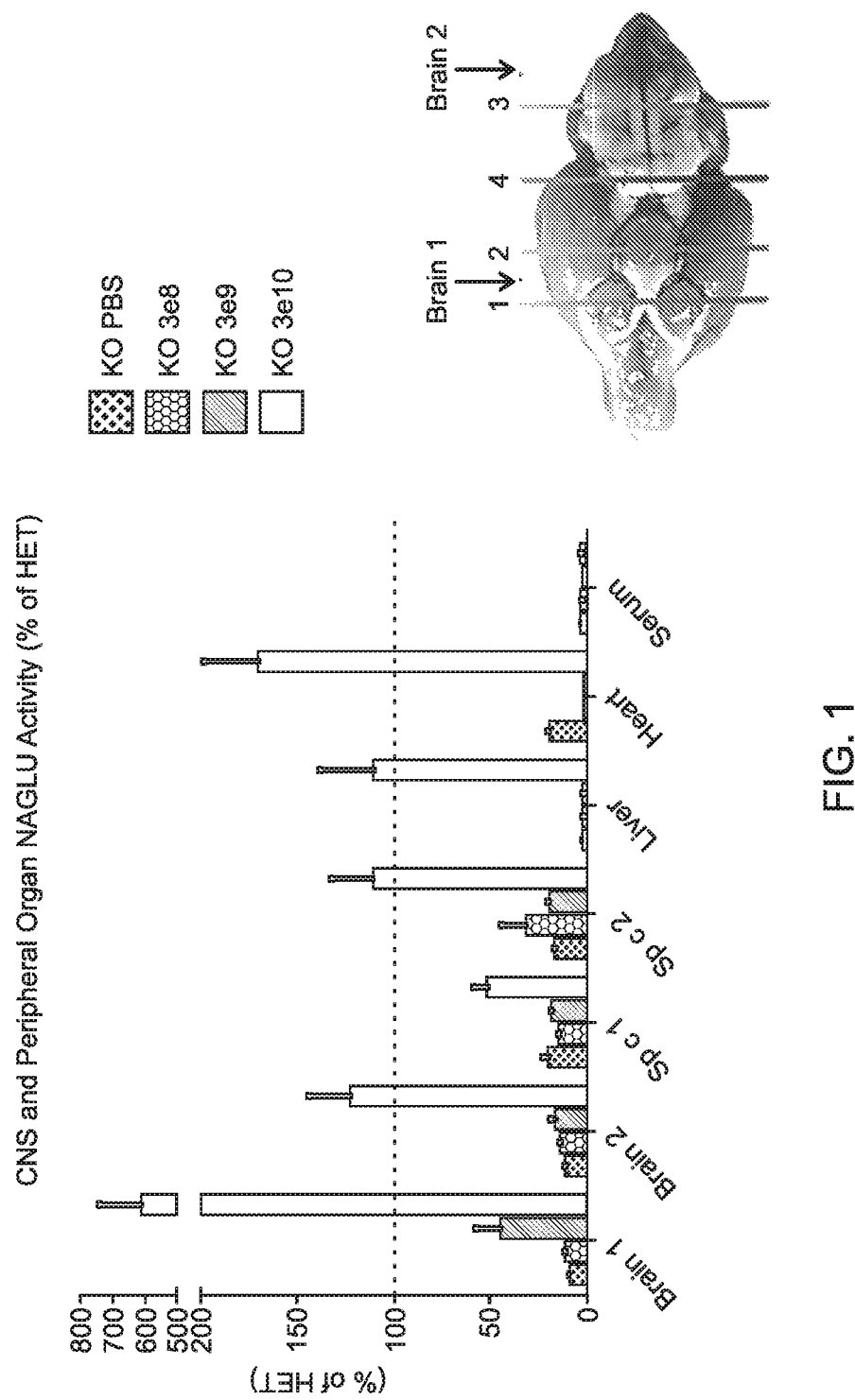
FIG. 1 illustrates that there is NAGLU activity in brain, spinal cord, liver, heart, and serum 3 months after intracerebroventricular (icy) administration of AAV9.CB7.CI.NAGLUco.rBG. There is a dose dependent increase in NAGLU activity in the brain, spinal cord, liver, and heart. There is essentially no activity in the low dose animals, partial rescue in the mid dose, and activity levels equal or above the heterozygous in all organs from the high dose treated animals. Activity in the serum is very low due to the presence of anti hNAGLU circulating antibodies.

Compositions useful for the treatment of Mucopolysaccharidosis type Mb (MPS IIIB) and/or alleviating symptoms of MPSIIIB are provided herein. These compositions comprise a nucleic acid sequence encoding a functional human N-acetyl-alpha-D-glucosaminidase (hNAGLU) and a regulatory sequence which direct expression thereof in a target cell, wherein the hNAGLU coding sequence is at least 95% identical to SEQ ID NO: 1.

In one embodiment, the compositions and methods described herein involve nucleic acid sequences, expression cassettes, vectors, recombinant viruses, other compositions and methods for expression of a functional human NAGLU (hNAGLU). In another embodiment, the compositions and methods described herein involve nucleic acid sequences, expression cassettes, vectors, recombinant viruses, host cells, other compositions and methods for production of a composition comprising the nucleic acid sequence encoding a functional hNAGLU. In yet another embodiment, the compositions and methods described herein involve nucleic acid sequences, expression cassettes, vectors, recombinant viruses, other compositions and methods for delivery of the nucleic acid sequence encoding a functional hNAGLU to a subject for the treatment of MPS IIIB. In one embodiment, the compositions and methods described herein are useful for providing a therapeutic level of NAGLU into the central nervous system (CNS). Additionally or alternatively, the compositions and methods described herein are useful for providing a therapeutic level of NAGLU in the periphery, such as, e.g., blood, liver, kidney, or peripheral nervous system. In certain embodiments, an adeno-associated viral (AAV) vector-based method described herein provides a new treatment option, helping to restore a desired function of NAGLU, to alleviate a symptom associated with MPS IIIB, to improve MPS IIIB-related biomarkers, or to facilitate other treatment(s) for MPS IIIB, by providing expression of NAGLU protein in a subject in need.

As used herein, the term "a therapeutic level" means an enzyme activity at least about 5%, about 8%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, more than 100%, about 2-fold, about 3-fold, or about 5-fold of a healthy control. Suitable assays for measuring NAGLU enzymatic activity are described herein. In some embodiments, such therapeutic levels of NAGLU may result in alleviation of the MPS IIIB related symptom(s); improvement of MPS IIIB-related biomarkers of disease; or facilitation of other treatment(s) for MPS IIIB, e.g., GAG levels in the cerebrospinal fluid (CSF), serum, urine or any other biological samples; prevention of neurocognitive decline; reversal of certain MPS IIIB-related symptoms and/or prevention of progression of MPS IIIB-related certain symptoms; or any combination thereof.

As used herein, "a healthy control" refers to a subject or a biological sample therefrom, wherein the subject does not have an MPS disorder. The healthy control can be from one subject. In another embodiment, the healthy control is a pool of multiple subjects.

As used herein, the term "biological sample" refers to any cell, biological fluid or tissue. Suitable samples for use in this invention may include, without limitation, whole blood, leukocytes, fibroblasts, serum, urine, plasma, saliva, bone marrow, cerebrospinal fluid, amniotic fluid, and skin cells. Such samples may further be diluted with saline, buffer or a physiologically acceptable diluent. Alternatively, such samples are concentrated by conventional means.

With regard to the description of these inventions, it is intended that each of the compositions herein described, is useful, in another embodiment, in the methods of the invention. In addition, it is also intended that each of the compositions herein described as useful in the methods, is, in another embodiment, itself an embodiment of the invention.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

As used herein, "disease", "disorder" and "condition" are Mucopolysaccharidosis type IIIb (MPS IIIB, MPS IIIb, also known as Sanfilippo syndrome type B or Sanfilippo type B disease).

As used herein, the term "MPS IIIB-related symptom(s)" or "symptom(s)" refers to symptom(s) found in MPS MB patients as well as in MPS IIIB animal models. Such symptoms include but not limited to delayed speech; difficulty with social interactions and communication; sleep disturbances; progressive intellectual disability and the loss of previously acquired skills (developmental regression); seizures and movement disorders; a large head; a slightly enlarged liver (mild hepatomegaly); a soft out-pouching around the belly-button (umbilical hernia) or lower abdomen (inguinal hernia); short stature, joint stiffness, mild dysostosis multiplex, multiple skeletal abnormalities; chronic diarrhea; recurrent upper respiratory infections; recurrent ear infections; hearing impairment; vision problems; Asymmetric septal hypertrophy; Coarse facial features; Coarse hair; Dense calvaria; Dysostosis multiplex; Growth abnormality; Heparan sulfate excretion in urine; GAG accumulation in the cerebrospinal fluid (CSF), serum, urine and/or other biological samples; abnormal expression and/or enzyme activity of N-sulfoglycosamine sulfohydrolase (SGSH) or N-sulfoglycosamine sulfohydrolase (IDUA); accumulation of GM2 and GM3; changed activity in lysosomal enzymes; accumulation of free unesterified cholesterol in the CNS; inflammatory response in the CNS and skeletal tissues; excess hair growth (Hirsutism); Hyperactivity; Ovoid thoracolumbar vertebrae; Splenomegaly; Synophrys; Thickened ribs; hernias; and a wobbly and erratic walk.

"Patient" or "subject" as used herein means a male or female human, dogs, and animal models used for clinical research. In one embodiment, the subject of these methods and compositions is a human diagnosed with MPS IIIB. In certain embodiments, the human subject of these methods and compositions is a prenatal, a newborn, an infant, a toddler, a preschool, a grade-schooler, a teen, a young adult or an adult. In a further embodiment, the subject of these methods and compositions is a pediatric MPS IIIB patient.

Clinical examination and urine tests (excess mucopolysaccharides are excreted in the urine) are the first steps in the diagnosis of an MPS disease. Enzyme assays measuring levels of enzyme activity in the blood, skin cells or a variety of cells are also used to provide definitive diagnosis of MPS TIM. See, www_ncbi_nlm_nih_gov/gtr/all/tests/?term=4669[geneid]; and www_ncbi_nlm_nih_gov/gtr/all/tests/?term=C0086648-[DISCUI]&filter=method:1_2;testtype:clinical. Various genetic testing detecting a mutation of NAGLU associated with MPS IIIB is available. See, e.g., www_ncbi_nlm_nih_gov/gtr/conditions/C0086648/; www_ncbi_nlm_nih_gov/gtr/all/tests/?term=C0086648[DISCUI]&filter=method:2_7;testtype:clinical; and www_ncbi_nlm_nih_gov/gtr/tests/506481/. Prenatal diagnosis using amniocentesis and chorionic villus sampling can verify if a fetus is affected with the disorder. Genetic counseling can help parents who have a family history of the mucopolysaccharidoses determine if they are carrying the mutated gene that causes the disorders. See, e.g., A Guide to Understanding MPS III, National MPS Society, 2008, mpssociety_org/learn/diseases/mpsiii/.

"Comprising" is a term meaning inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention. It should be understood that while various embodiments in the specification are presented using "comprising" language, under various circumstances, a related embodiment is also described using "consisting of" or "consisting essentially of" language.

It is to be noted that the term "a" or "an", refers to one or more, for example, "a vector", is understood to represent one or more vector(s). As such, the terms "a" (or "an"), "one or more", and "at least one" is used interchangeably herein.

As used herein, the term "about" means a variability of plus or minus 10% from the reference given, unless otherwise specified.

1. N-acetyl-alpha-glucosaminidase (NAGLU)

As used herein, the terms "N-acetyl-alpha-glucosaminidase", "NAGLU" and "NaGlu" are used interchangeably with "Alpha-N-Acetylglucosaminidase". The invention includes any variant of NAGLU protein expressed from the nucleic acid sequences provided herein, or a functional fragment thereof, which restores a desired function, ameliorates a symptom, improves symptoms associated with a MPS IIIB-related biomarker, or facilitates other treatment(s) for MPS IIIB when delivered in a composition or by a method as provided herein. Examples of a suitable biomarker for MPSIII include that described in WO 2017/136533, which is incorporated herein by reference.

As used herein, the term "functional NAGLU" means an enzyme having the amino acid sequence of the full-length wild-type (native) human NAGLU (as shown in SEQ ID NO: 2 and UniProtKB accession number: P54802), a variant thereof, a mutant thereof with a conservative amino acid replacement, a fragment thereof, a full-length or a fragment of any combination of the variant and the mutant with a conservative amino acid replacement, which provides at least about 10%, at least about 20%, at least about 30%, at least about 40%, at least about 50%, at least about 60%, at least about 70%, at least about 75%, at least about 80%, at least about 90%, or about the same, or greater than 100% of the biological activity level of normal human NAGLU. In one embodiment, a functional NAGLU refers to a wild-type NAGLU protein with sequence of SEQ ID NO: 2.

Examples of NAGLU variants include but not limited to, E705K, which consists of the amino acid sequence of SEQ ID NO: 2 with a Lysine (Lys, K) at the 705th amino acid instead of Glutamic acid (Glu, E) in the wild-type.

As used herein, the "conservative amino acid replacement" or "conservative amino acid substitutions" refers to a change, replacement or substitution of an amino acid to a different amino acid with similar biochemical properties (e.g. charge, hydrophobicity and size), which is known by practitioners of the art. Also see, e.g. French et al. What is a conservative substitution? Journal of Molecular Evolution, March 1983, Volume 19, Issue 2, pp 171-175 and YAMPOLSKY et al. The Exchangeability of Amino Acids in Proteins, Genetics. 2005 August; 170(4): 1459-1472, each of which is incorporated herein by reference in its entirety.

A variety of assays exist for measuring NAGLU expression and activity levels by conventional methods. See, e.g., Example 1 as described herein; www_ncbi_nlm_nih_gov/gtr/all/tests/?term=C0086648[DISCUI]&filter=method:1_2;test type:clinical;www_ncbi_nlm_nih_gov/gtr/all/tests/?term=C0086648[DISCUI]&filter=method:1_1;testtype:clinical; Kan S H et al, Delivery of an enzyme-IGFII fusion protein to the mouse brain is therapeutic for mucopolysaccharidosis type IIIB. Proc Natl Acad Sci USA. 2014 Oct. 14; 111(41):14870-5. doi: 10.1073/pnas.1416660111. Epub 2014 Sep. 29; US 2017/0088859; each of which is incorporated by reference herein in its entirety.

In one aspect, a nucleic acid sequence which encodes a functional NAGLU protein is provided. In one embodiment, the nucleic acid sequence is the wild-type coding sequence reproduced in SEQ ID NO: 3. In one embodiment, the nucleic acid sequence is at least about 60%, at least about 65%, at least about 70%, at least about 75%, at least about 80% identical thereto the wild-type human NAGLU sequence of SEQ ID NO: 3.

A nucleic acid refers to a polymeric form of nucleotides and includes RNA, mRNA, cDNA, genomic DNA, peptide nucleic acid (PNA) and synthetic forms and mixed polymers of the above. A nucleotide refers to a ribonucleotide, deoxynucleotide or a modified form of either type of nucleotide (e.g., a peptide nucleic acid oligomer). The term also includes single- and double-stranded forms of DNA. The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules.

In certain embodiments, the nucleic acid molecules encoding a functional human NAGLU (hNAGLU), and other constructs encompassed by the present invention and useful in generating expression cassettes and vector genomes may be engineered for expression in yeast cells, insect cells or mammalian cells, such as human cells. Methods are known and have been described previously (e.g. WO 96/09378). A sequence is considered engineered if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in www.kazusa.jp/codon. Preferably more than one non-preferred codon, preferably most or all non-preferred codons, are replaced by codons that are more preferred. Preferably the most frequently used codons in an organism are used in an engineered sequence. Replacement by preferred codons generally leads to higher expression. It will also be understood by a skilled person that numerous different nucleic acid molecules can encode the same polypeptide as a result of the degeneracy of the genetic code. It is also understood that skilled persons may, using routine techniques, make nucleotide substitutions that do not affect the amino acid sequence encoded by the nucleic acid molecules to reflect the codon usage of any particular host organism in which the polypeptides are to be expressed. Therefore, unless otherwise specified, a "nucleic acid sequence encoding an amino acid sequence" includes all nucleotide sequences that are degenerate versions of each other and that encode the same amino acid sequence. Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScript, Life Technologies, Eurofins).

In one aspect, the NAGLU coding sequence is an engineered sequence. In one embodiment, the engineered sequence is useful to improve production, transcription, expression or safety in a subject. In another embodiment, the engineered sequence is useful to increase efficacy of the resulting therapeutic compositions or treatment. In a further embodiment, the engineered sequence is useful to increase the efficacy of the functional NAGLU protein being expressed, but may also permit a lower dose of a therapeutic reagent that delivers the functional protein to increase safety.

In one embodiment, the engineered NAGLU coding sequence is characterized by improved translation rate as compared to wild-type NAGLU coding sequences. In one embodiment, the NAGLU coding sequence has less than 82% identical to the wild-type hNAGLU sequence of SEQ ID NO: 3. In one embodiment, the NAGLU coding sequence shares less than about 99%, less than about 98%, less than about 97%, less than about 96%, less than about 95%, less than about 94%, less than about 93%, less than about 92%, less than about 91%, less than about 90%, less than about 89%, less than about 88%, less than about 87%, less than about 86%, less than about 85%, less than about 84%, less than about 83%, less than about 82%, less than about 81%, less than about 80%, less than about 79%, less than about 78%, less than about 77%, less than about 76%, less than about 75%, less than about 74%, less than about 73%, less than about 72%, less than about 71%, less than about 70%, less than about 69%, less than about 68%, less than about 67%, less than about 66%, less than about 65%, less than about 64%, less than about 63%, less than about 62%, less than about 61% or less identity to the wild type NAGLU coding sequence. In another embodiment, the NAGLU coding sequence shares about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61% or less identity to the wild type NAGLU coding sequence. In one embodiment, provided is an engineered nucleic acid sequence comprising a sequence of SEQ ID NO: 1. In one embodiment, provided herein is an engineered nucleic acid sequence of SEQ ID NO: 1, or a nucleic acid sequence at least about 95% identical thereto, encoding a functional hNAGLU. In another embodiment, the NAGLU coding sequence is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identity to SEQ ID NO: 1, wherein the sequence encodes a functional hNAGLU.

By "engineered" is meant that the nucleic acid sequences encoding a functional NAGLU protein described herein are assembled and placed into any suitable genetic element, e.g., naked DNA, phage, transposon, cosmid, episome, etc., which transfers the NAGLU sequences carried thereon to a host cell, e.g., for generating non-viral delivery systems (e.g., RNA-based systems, naked DNA, or the like), or for generating viral vectors in a packaging host cell, and/or for delivery to a host cells in a subject. In one embodiment, the genetic element is a vector. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Multiple sequence alignment programs are also available for nucleic acid sequences. Examples of such programs include, "Clustal Omega", "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Identity may be determined by preparing an alignment of the sequences and through the use of a variety of algorithms and/or computer programs known in the art or commercially available (e.g., BLAST, ExPASy; Clustal Omega; FASTA; using, e.g., Needleman-Wunsch algorithm, Smith-Waterman algorithm). Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, "a desired function" refers to an NAGLU enzyme activity at least 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or greater than 100% of a healthy control.

As used herein, the phrases "ameliorate a symptom", "improve a symptom" or any grammatical variants thereof, refer to reversal of an MPS IIIB-related symptoms, showdown or prevention of progression of an MPS IIIB-related symptoms. In one embodiment, the amelioration or improvement refers to the total number of symptoms in a patient after administration of the described composition(s) or use of the described method, which is reduced by about 5%, about 10%, about 20%, about 30%, about 40%, about 50%, about 60%, about 70%, about 80%, about 90%, about 95% compared to that before the administration or use. In another embodiment, the amelioration or improvement refers to the severity or progression of a symptom after administration of the described composition(s) or use of the described method, which is reduced by about 5%, about 10%, about 20%, about 30%, about 40%, about 50%, about 60%, about 70%, about 80%, about 90%, about 95% compared to that before the administration or use.

It should be understood that the compositions in the functional NAGLU protein and NAGLU coding sequence described herein are intended to be applied to other compositions, regiments, aspects, embodiments and methods described across the Specification.

2. Expression Cassette

In one aspect, provided is an expression cassette comprising an engineered nucleic acid sequence encoding a functional hNAGLU, and a regulatory sequence which direct expression thereof. In one embodiment, an expression cassette comprising an engineered nucleic acid sequence as described herein which encodes a functional hNAGLU, and a regulatory sequence which direct expression thereof. In one embodiment, the hNAGLU coding sequence is at least 95% identical to SEQ ID NO: 1. In a further embodiment, the hNAGLU coding sequence is SEQ ID NO: 1. In one embodiment, the regulatory sequence comprises a promoter. In a further embodiment, the regulatory sequence comprises a CB7 promoter. In one embodiment, the regulatory sequence further comprises a chicken beta-actin intron. In one embodiment, the regulatory sequence further comprises a rabbit globin poly A.

As used herein, the term "expression" or "gene expression" refers to the process by which information from a gene is used in the synthesis of a functional gene product. The gene product may be a protein, a peptide, or a nucleic acid polymer (such as a RNA, a DNA or a PNA).

As used herein, an "expression cassette" refers to a nucleic acid polymer which comprises the coding sequences for a functional hNAGLU, promoter, and may include other regulatory sequences therefor, which cassette may be packaged into a vector.

As used herein, the term "regulatory sequence", or "expression control sequence" refers to nucleic acid sequences, such as initiator sequences, enhancer sequences, and promoter sequences, which induce, repress, or otherwise control the transcription of protein encoding nucleic acid sequences to which they are operably linked.

As used herein, the term "operably linked" refers to both expression control sequences that are contiguous with the nucleic acid sequence encoding the functional hNAGLU and/or expression control sequences that act in trans or at a distance to control the transcription and expression thereof.

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

In one embodiment, the regulatory sequence comprises a promoter. In one embodiment, the promoter is a chicken β-actin promoter. In a further embodiment, the promoter is a hybrid of a cytomegalovirus immediate-early enhancer and the chicken β-actin promoter (a CB7 promoter). In another embodiment, a suitable promoter may include without limitation, an elongation factor 1 alpha (EF1 alpha) promoter (see, e.g., Kim D W et al, Use of the human elongation factor 1 alpha promoter as a versatile and efficient expression system. Gene. 1990 Jul. 16; 91(2):217-23), a Synapsin 1 promoter (see, e.g., Kugler S et al, Human synapsin 1 gene promoter confers highly neuron-specific long-term transgene expression from an adenoviral vector in the adult rat brain depending on the transduced area. Gene Ther. 2003 February; 10(4):337-47), a neuron-specific enolase (NSE) promoter (see, e.g., Kim J et al, Involvement of cholesterol-rich lipid rafts in interleukin-6-induced neuroendocrine differentiation of LNCaP prostate cancer cells. Endocrinology. 2004 February; 145(2):613-9. Epub 2003 Oct. 16), or a CB6 promoter (see, e.g., Large-Scale Production of Adeno-Associated Viral Vector Serotype-9 Carrying the Human Survival Motor Neuron Gene, Mol Biotechnol. 2016 January; 58(1):30-6. doi: 10.1007/s12033-015-9899-5).

In one embodiment, the expression cassette is designed for expression and secretion in a human subject. In one embodiment, the expression cassette is designed for expression in the central nervous system (CNS), including the cerebral spinal fluid and brain. In a further embodiment, the expression cassette is useful for expression in both the CNS and in the liver. Suitable promoters may be selected, including but not limited to a constitutive promoter, a tissue-specific promoter or an inducible/regulatory promoter. Example of a constitutive promoter is chicken beta-actin promoter. A variety of chicken beta-actin promoters have been described alone, or in combination with various enhancer elements (e.g., CB7 is a chicken beta-actin promoter with cytomegalovirus enhancer elements; a CAG promoter, which includes the promoter, the first exon and first intron of chicken beta actin, and the splice acceptor of the rabbit beta-globin gene; a CBh promoter, S J Gray et al, Hu Gene Ther, 2011 September; 22(9): 1143-1153). Examples of promoters that are tissue-specific are well known for liver (albumin, Miyatake et al., (1997) *J. Virol.*, 71:5124-32; hepatitis B virus core promoter, Sandig et al., (1996) *Gene Ther.*, 3:1002-9; alpha-fetoprotein (AFP), Arbuthnot et al., (1996) *Hum. Gene Ther.*, 7:1503-14), neuron (such as neuron-specific enolase (NSE) promoter, Andersen et al., (1993) *Cell. Mol. Neurobiol.*, 13:503-15; neurofilament light-chain gene, Piccioli et al., (1991) *Proc. Natl. Acad. Sci. USA,* 88:5611-5; and the neuron-specific vgf gene, Piccioli et al., (1995) *Neuron,* 15:373-84), and other tissues. Alternatively, a regulatable promoter may be selected. See, e.g., WO 2011/126808B2, incorporated by reference herein.

In one embodiment, the regulatory sequence further comprises an enhancer. In one embodiment, the regulatory sequence comprises one enhancer. In another embodiment, the regulatory sequence contains two or more expression enhancers. These enhancers may be the same or may be different. For example, an enhancer may include an Alpha mic/bik enhancer or a CMV enhancer. This enhancer may be present in two copies which are located adjacent to one another. Alternatively, the dual copies of the enhancer may be separated by one or more sequences.

In one embodiment, the regulatory sequence further comprises an intron. In a further embodiment, the intron is a chicken beta-actin intron. Other suitable introns include those known in the art may by a human β-globulin intron, and/or a commercially available Promega® intron, and those described in WO 2011/126808.

In one embodiment, the regulatory sequence further comprises a Polyadenylation signal (polyA). In a further embodiment, the polyA is a rabbit globin poly A. See, e.g., WO 2014/151341. Alternatively, another polyA, e.g., a human growth hormone (hGH) polyadenylation sequence, an SV40 polyA, or a synthetic polyA may be included in an expression cassette.

It should be understood that the compositions in the expression cassette described herein are intended to be applied to other compositions, regiments, aspects, embodiments and methods described across the Specification.

3. Vector

In one aspect, provided herein is a vector comprising an engineered nucleic acid sequence encoding a functional human NAGLU and a regulatory sequence which direct expression thereof in a target cell. In one embodiment, the hNAGLU coding sequence is at least 95% identical to SEQ ID NO: 1. In a further embodiment, the hNAGLU coding sequence is SEQ ID NO: 1.

A "vector" as used herein is a biological or chemical moiety comprising a nucleic acid sequence which can be introduced into an appropriate target cell for replication or expression of said nucleic acid sequence. Examples of a vector includes but not limited to a recombinant virus, a plasmid, Lipoplexes, a Polymersome, Polyplexes, a dendrimer, a cell penetrating peptide (CPP) conjugate, a magnetic particle, or a nanoparticle. In one embodiment, a vector is a nucleic acid molecule into which an exogenous or heterologous or engineered nucleic acid encoding a functional hNAGLU may be inserted, which can then be introduced into an appropriate target cell. Such vectors preferably have one or more origin of replication, and one or more site into which the recombinant DNA can be inserted. Vectors often have means by which cells with vectors can be selected from those without, e.g., they encode drug resistance genes. Common vectors include plasmids, viral genomes, and "artificial chromosomes". Conventional methods of generation, production, characterization or quantification of the vectors are available to one of skill in the art.

In one embodiment, the vector is a non-viral plasmid that comprises an expression cassette described thereof, e.g., "naked DNA", "naked plasmid DNA", RNA, and mRNA; coupled with various compositions and nano particles, including, e.g., micelles, liposomes, cationic lipid-nucleic acid compositions, poly-glycan compositions and other polymers, lipid and/or cholesterol-based-nucleic acid conjugates, and other constructs such as are described herein. See, e.g., X. Su et al, Mol. Pharmaceutics, 2011, 8 (3), pp 774-787; web publication: Mar. 21, 2011; WO2013/182683, WO 2010/053572 and WO 2012/170930, all of which are incorporated herein by reference.

In certain embodiments, the vector described herein is a "replication-defective virus" or a "viral vector" which refers to a synthetic or artificial viral particle in which an expression cassette containing a nucleic acid sequence encoding a functional hNAGLU is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the nucleic acid sequence encoding NAGLU flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

As used herein, a recombinant virus vector is an adeno-associated virus (AAV), an adenovirus, a bocavirus, a hybrid AAV/bocavirus, a herpes simplex virus or a lentivirus.

As used herein, the term "host cell" may refer to the packaging cell line in which a vector (e.g., a recombinant AAV) is produced. A host cell may be a prokaryotic or eukaryotic cell (e.g., human, insect, or yeast) that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. Examples of host cells may include, but are not limited to an isolated cell, a cell culture, an *Escherichia coli* cell, a yeast cell, a human cell, a non-human cell, a mammalian cell, a non-mammalian cell, an insect cell, an HEK-293 cell, a liver cell, a kidney cell, a cell of the central nervous system, a neuron, a glial cell, or a stem cell.

As used herein, the term "target cell" refers to any target cell in which expression of the functional NAGLU is desired. In certain embodiments, the term "target cell" is intended to reference the cells of the subject being treated for MPS MB. Examples of target cells may include, but are not limited to, a liver cell, a kidney cell, a cell of the central nervous system, a neuron, a glial cell, and a stem cell. In certain embodiments, the vector is delivered to a target cell ex vivo. In certain embodiments, the vector is delivered to the target cell in vivo.

It should be understood that the compositions in the vector described herein are intended to be applied to other compositions, regiments, aspects, embodiments and methods described across the Specification.

4. Adeno-Associated Virus (AAV)

In one aspect, provided herein is a recombinant AAV (rAAV) comprising an AAV capsid and a vector genome packaged therein. The rAAV is for use in the treatment of Mucopolysaccharidosis III B (MPS IIIB). The vector genome comprises an AAV 5' inverted terminal repeat (ITR), an engineered nucleic acid sequence encoding a functional hNAGLU as described herein, a regulatory sequence which direct expression of hNAGLU in a target cell, and an AAV 3' ITR. In one embodiment, the hNAGLU coding sequence is at least 95% identical to SEQ ID NO: 1. In a further embodiment, the hNAGLU coding sequence is SEQ ID NO: 1. In one embodiment, the regulatory sequence comprises a promoter. In a further embodiment, the regulatory sequence further comprises an enhancer. In one embodiment, the regulatory sequence further comprises an intron. In one embodiment, the regulatory sequence further comprises a poly A. In certain embodiments, the AAV vector genome comprises the sequence of SEQ ID NO: 4 (AAV.CB7.CI.hNAGLUco.RBG), which encodes the hNAGLU protein of SEQ ID NO: 5. In one embodiment, the AAV capsid is an AAV9 capsid. In one embodiment, the rAAV described herein is for use in the treatment of Mucopolysaccharidosis III B (MPS IIIB).

In one embodiment, the regulatory sequence is as described above. In one embodiment, the vector genome comprises an AAV 5' inverted terminal repeat (ITR), an expression cassette as described herein, and an AAV 3' ITR.

In one embodiment, provided is a rAAV comprising an AAV serotype 9 (AAV9) capsid and a vector genome comprising a CB7 promoter expressing an engineered version of hNAGLU with a rabbit beta-globin (rBG) polyA sequence. In a further embodiment, the rAAV vector genome comprises the sequence of SEQ ID NO: 4 (AAV.CB7.CI.hSNAGLUco.rBG). In one embodiment, the rAAV comprises an AAV9 capsid and a vector genome comprising the sequence of SEQ ID NO: 4, wherein the rAAV is represented as AAV9.CB7.CI.hSNAGLUco.rBG.

As used herein, a "vector genome" refers to the nucleic acid sequence packaged inside a vector. In one embodiment, the vector genome refers to the nucleic acid sequence packaged inside a rAAV capsid forming an rAAV vector. Such a nucleic acid sequence contains AAV inverted terminal repeat sequences (ITRs). In one example, a vector genome contains, at a minimum, from 5' to 3', an AAV2 5' ITR, a nucleic acid sequence encoding a functional NAGLU, and an AAV2 3' ITR. However, ITRs from a different source AAV other than AAV2 may be selected. Further, other ITRs may be used. Further, the vector genome contains regulatory sequences which direct expression of the functional NAGLU.

The ITRs are the genetic elements responsible for the replication and packaging of the genome during vector production and are the only viral cis elements required to generate rAAV. In one embodiment, the ITRs are from an AAV different than that supplying a capsid. In a preferred embodiment, the ITR sequences from AAV2, or the deleted version thereof (ΔITR), which may be used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, AAV vector genome comprises an AAV 5' ITR, the NAGLU coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The term "AAV" as used herein refers to naturally occurring adeno-associated viruses, adeno-associated viruses available to one of skill in the art and/or in light of the composition(s) and method(s) described herein, as well as artificial AAVs. An adeno-associated virus (AAV) viral vector is an AAV DNase-resistant particle having an AAV protein capsid into which is packaged expression cassette flanked by AAV inverted terminal repeat sequences (ITRs) for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. Various AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111

(AAV9), and WO 2006/110689, and WO 2003/042397 (rh.10). These documents also describe other AAV which may be selected for generating AAV and are incorporated by reference. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, the AAVs commonly identified as AAV1, AAV2, AAV3, AAV4, AAV5, AAV6, AAV7, AAV8, AAV9, AAV8bp, AAV7M8 and AAVAnc80, variants of any of the known or mentioned AAVs or AAVs yet to be discovered or variants or mixtures thereof. See, e.g., WO 2005/033321, which is incorporated herein by reference. In one embodiment, the AAV capsid is an AAV9 capsid or variant thereof. In certain embodiments, the capsid protein is designated by a number or a combination of numbers and letters following the term "AAV" in the name of the rAAV vector. In one embodiment, provided is a rAAV (AAV9.CB7.CI.hSNAGLUco.rBG) comprising an AAV serotype 9 (AAV9) capsid and a vector genome comprising the sequence of SEQ ID NO: 4 (AAV.CB7.CI.hSNAGLUco.rBG).

As used herein, relating to AAV, the term "variant" means any AAV sequence which is derived from a known AAV sequence, including those with a conservative amino acid replacement, and those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3).

The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, Va.). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

As used herein, the terms "rAAV" and "artificial AAV" used interchangeably, mean, without limitation, a AAV comprising a capsid protein and a vector genome packaged therein, wherein the vector genome comprising a nucleic acid heterologous to the AAV. In one embodiment, the capsid protein is a non-naturally occurring capsid. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, "AAV9 capsid" refers to the AAV9 having the amino acid sequence of (a) GenBank accession: AAS99264, is incorporated by reference herein and the AAV vp1 capsid protein is reproduced in SEQ ID NO: 6, and/or (b) the amino acid sequence encoded by the nucleotide sequence of GenBank Accession: AY530579.1: (nt 1 . . . 2211) (reproduced in SEQ ID NO: 7). Some variation from this encoded sequence is encompassed by the present invention, which may include sequences having about 99% identity to the referenced amino acid sequence in GenBank accession: AAS99264 and US7906111 (also WO 2005/033321) (i.e., less than about 1% variation from the referenced sequence). Such AAV may include, e.g., natural isolates (e.g., hu68 (described in co-pending U.S. Patent Applications No. 62/464,748, filed Feb. 28, 2017 and U.S. Patent Application No. 62/591,002, filed Nov. 27, 2019, both entitled "Novel Adeno-associated virus (AAV) Clade F Vector and Uses Therefor" and WO 2018/160582), hu31 or hu32), or variants of AAV9 having amino acid substitutions, deletions or additions, e.g., including but not limited to amino acid substitutions selected from alternate residues "recruited" from the corresponding position in any other AAV capsid aligned with the AAV9 capsid; e.g., such as described in U.S. Pat. Nos. 9,102,949, 8,927,514, US2015/349911; WO 2016/049230A11; U.S. Pat. Nos. 9,623,120; 9,585,971. However, in other embodiments, other variants of AAV9, or AAV9 capsids having at least about 95% identity to the above-referenced sequences may be selected. See, e.g., US Published Patent Application No. 2015/0079038. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, the rAAV as described herein is a self-complementary AAV. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

In certain embodiments, the rAAV described herein is nuclease-resistant. Such nuclease may be a single nuclease, or mixtures of nucleases, and may be endonucleases or exonucleases. A nuclease-resistant rAAV indicates that the AAV capsid has fully assembled and protects these packaged genomic sequences from degradation (digestion) during nuclease incubation steps designed to remove contaminating nucleic acids which may be present from the production process. In many instances, the rAAV described herein is DNase resistant.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid; a functional rep gene; an expression cassette as described herein flanked by AAV inverted terminal repeats (ITRs); and sufficient helper functions to permit packaging of the expression cassette into the AAV capsid protein. Also provided herein is the host cell which contains a nucleic acid sequence encoding an AAV capsid; a functional rep gene; a vector genome as described; and sufficient helper functions to permit packaging of the vector genome into the AAV capsid protein. In one embodiment, the host cell is a HEK 293 cell. These methods are described in more detail in WO2017160360 A2, which is incorporated by reference herein.

Other methods of producing rAAV available to one of skill in the art may be utilized. Suitable methods may include without limitation, baculovirus expression system or production via yeast. See, e.g., Robert M. Kotin, Large-scale recombinant adeno-associated virus production. Hum Mol Genet. 2011 Apr. 15; 20(R1): R2-R6. Published online 2011 Apr. 29. doi: 10.1093/hmg/ddr141; Aucoin M G et al., Production of adeno-associated viral vectors in insect cells using triple infection: optimization of baculovirus concentration ratios. Biotechnol Bioeng. 2006 Dec. 20; 95(6):1081-92; SAMI S. THAKUR, Production of Recombinant Adeno-associated viral vectors in yeast. Thesis presented to the Graduate School of the University of Florida, 2012; Kondratov O et al. Direct Head-to-Head Evaluation of Recombinant Adeno-associated Viral Vectors Manufactured in Human versus Insect Cells, Mol Ther. 2017 Aug. 10. pii: 51525-0016(17)30362-3. doi: 10.1016/j.ymthe.2017.08.003. [Epub ahead of print]; Mietzsch M et al, OneBac 2.0: Sf9 Cell Lines for Production of AAV1, AAV2, and AAV8 Vectors with Minimal Encapsidation of Foreign DNA. Hum Gene Ther Methods. 2017 February; 28(1):15-22. doi: 10.1089/hgtb.2016.164.; Li L et al. Production and characterization of novel recombinant adeno-associated virus replicative-form genomes: a eukaryotic source of DNA for gene transfer. PLoS One. 2013 Aug. 1; 8(8):e69879. doi: 10.1371/journal.pone.0069879. Print 2013; Galibert L et al, Latest developments in the large-scale production of adeno-associated virus vectors in insect cells toward the treatment of neuromuscular diseases. J Invertebr Pathol. 2011 July; 107 Suppl:S80-93. doi: 10.1016/j.jip.2011.05.008; and Kotin R M, Large-scale recombinant adeno-associated virus production. Hum Mol Genet. 2011 Apr. 15; 20(R1):R2-6. doi: 10.1093/hmg/ddr141. Epub 2011 Apr. 29.

A two-step affinity chromatography purification at high salt concentration followed by anion exchange resin chromatography are used to purify the vector drug product and to remove empty capsids. These methods are described in more detail in WO 2017/160360 entitled "Scalable Purification Method for AAV9", which is incorporated by reference herein. In brief, the method for separating rAAV9 particles having packaged genomic sequences from genome-deficient AAV9 intermediates involves subjecting a suspension comprising recombinant AAV9 viral particles and AAV 9 capsid intermediates to fast performance liquid chromatography, wherein the AAV9 viral particles and AAV9 intermediates are bound to a strong anion exchange resin equilibrated at a pH of 10.2, and subjected to a salt gradient while monitoring eluate for ultraviolet absorbance at about 260 and about 280. Although less optimal for rAAV9, the pH may be in the range of about 10.0 to 10.4. In this method, the AAV9 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured.

Conventional methods for characterization or quantification of rAAV are available to one of skill in the art. To calculate empty and full particle content, VP3 band volumes for a selected sample (e.g., in examples herein an iodixanol gradient-purified preparation where # of GC=# of particles) are plotted against GC particles loaded. The resulting linear equation ($y=mx+c$) is used to calculate the number of particles in the band volumes of the test article peaks. The number of particles (pt) per 20 µL, loaded is then multiplied by 50 to give particles (pt)/mL. Pt/mL divided by GC/mL gives the ratio of particles to genome copies (pt/GC). Pt/mL−GC/mL gives empty pt/mL. Empty pt/mL divided by pt/mL and ×100 gives the percentage of empty particles. Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Viral. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000-fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

Methods for determining the ratio among vp 1, vp2 and vp3 of capsid protein are also available. See, e.g., Vamseedhar Rayaprolu et al, Comparative Analysis of Adeno-Associated Virus Capsid Stability and Dynamics, J Virol. 2013 December; 87(24): 13150-13160; Buller R M, Rose J A. 1978. Characterization of adenovirus-associated virus-induced polypeptides in KB cells. J. Virol. 25:331-338; and Rose J A, Maizel J V, Inman J K, Shatkin A J. 1971. Structural proteins of adenovirus-associated viruses. J. Virol. 8:766-770.

As used herein, the term "treatment" or "treating" refers to composition(s) and/or method(s) for the purposes of amelioration of one or more symptoms of MPS IIIB, restore of a desired function of NAGLU, or improvement of biomarker of disease. In some embodiments, the term "treatment" or "treating" is defined encompassing administering to a subject one or more compositions described herein for the purposes indicated herein. "Treatment" can thus include one or more of reducing onset or progression of MPS IIIB, preventing disease, reducing the severity of the disease symptoms, retarding their progression, removing the disease symptoms, delaying progression of disease, or increasing efficacy of therapy in a given subject.

It should be understood that the compositions in the rAAV described herein are intended to be applied to other compositions, regiments, aspects, embodiments and methods described across the Specification.

5. Pharmaceutical Composition

In one aspect, provided herein is a pharmaceutical composition comprising a vector as described herein in a formulation buffer. In one embodiment, the pharmaceutical composition is suitable for co-administering with a functional hNAGLU protein or a protein comprising a functional hNAGLU. In one embodiment, provided is a pharmaceutical composition comprising a rAAV as described herein in a formulation buffer. In one embodiment, the rAAV is formulated at about $1 \times 10^9$ genome copies (GC)/mL to about $1 \times 10^{14}$ GC/mL. In a further embodiment, the rAAV is formulated at about $3 \times 10^9$ GC/mL to about $3 \times 10^{13}$ GC/mL. In yet a further embodiment, the rAAV is formulated at about $1 \times 10^9$ GC/mL to about $1 \times 10^{13}$ GC/mL. In one embodiment, the rAAV is formulated at least about $1 \times 10^{11}$ GC/mL.

In one embodiment, the formulation further comprises a surfactant, preservative, excipients, and/or buffer dissolved in the aqueous suspending liquid. In one embodiment, the buffer is PBS. In another embodiment, the buffer is an artificial cerebrospinal fluid (aCSF), e.g., Eliott's formulation buffer; or Harvard apparatus perfusion fluid (an artificial CSF with final Ion Concentrations (in mM): Na 150; K 3.0; Ca 1.4; Mg 0.8; P 1.0; Cl 155). Various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

Suitably, the formulation is adjusted to a physiologically acceptable pH, e.g., in the range of pH 6 to 8, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of 6.8 to about 7.2 may be desired. However, other pHs within the broadest ranges and these subranges may be selected for other route of delivery.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly (propylene oxide)) flanked by two hydrophilic chains of polyoxyethylene (poly (ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate.7H2O), potassium chloride, calcium chloride (e.g., calcium chloride.2H2O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical].

In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA Additionally provided is a pharmaceutical composition comprising a pharmaceutically acceptable carrier and a vector comprising a nucleic acid sequence encoding a functional NAGLU as described herein. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. Delivery vehicles such as liposomes, nanocapsules, microparticles, microspheres, lipid particles, vesicles, and the like, may be used for the introduction of the compositions of the present invention into suitable host cells. In particular, the rAAV vector may be formulated for delivery either encapsulated in a lipid particle, a liposome, a vesicle, a nanosphere, or a nanoparticle or the like. In one embodiment, a therapeutically effective amount of said vector is included in the pharmaceutical composition. The selection of the carrier is not a limitation of the present invention. Other conventional pharmaceutically acceptable carrier, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The phrase "pharmaceutically-acceptable" refers to molecular entities and compositions that do not produce an allergic or similar untoward reaction when administered to a host.

As used herein, the term "dosage" or "amount" can refer to the total dosage or amount delivered to the subject in the course of treatment, or the dosage or amount delivered in a single unit (or multiple unit or split dosage) administration.

Also, the replication-defective virus compositions can be formulated in dosage units to contain an amount of replication-defective virus that is in the range of about $1.0 \times 10^9$ GC to about $1.0 \times 10^{16}$ GC (to treat an average subject of 70 kg in body weight) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

In one embodiment, the pharmaceutical composition comprising a rAAV as described herein is administrable at a dose of about $1 \times 10^9$ GC per gram of brain mass to about $1 \times 10^{14}$ GC per gram of brain mass.

The aqueous suspension or pharmaceutical compositions described herein are designed for delivery to subjects in need thereof by any suitable route or a combination of different routes. In one embodiment, the pharmaceutical composition is formulated for delivery via intracerebroventricular (ICV), intrathecal (IT), or intracisternal injection. In one embodiment, the compositions described herein are designed for delivery to subjects in need thereof by intravenous injection. Alternatively, other routes of administration may be selected (e.g., oral, inhalation, intranasal, intratracheal, intraarterial, intraocular, intramuscular, and other parenteral routes).

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular, suboccipital/intracisternal, and/or C1-2 puncture. For example, material may be introduced for diffusion throughout the subarachnoid space by means of lumbar puncture. In another example, injection may be into the cisterna magna. Intracisternal delivery may increase vector diffusion and/or reduce toxicity and inflammation caused by the administration. See, e.g., Christian Hinderer et al, Widespread gene transfer in the central nervous system of cynomolgus macaques following delivery of AAV9 into the cisterna magna, Mol Ther Methods Clin Dev. 2014; 1: 14051. Published online 2014 Dec. 10. doi: 10.1038/mtm.2014.51.

As used herein, the terms "intracisternal delivery" or "intracisternal administration" refer to a route of administration for drugs directly into the cerebrospinal fluid of the brain ventricles or within the cisterna magna cerebellomedularis, more specifically via a suboccipital puncture or by direct injection into the cisterna magna or via permanently positioned tube. FIG. 6 provides an illustration as to how an intracisternal injection would be made.

It should be understood that the compositions in the pharmaceutical composition described herein are intended to be applied to other compositions, regiments, aspects, embodiments and methods described across the Specification.

6. Method of Treatment

In one aspect, provided herein is a method of treating a human subject diagnosed with MPS IIIB. Currently, when there is a clinical suspicion of MPS III, the first step is the request of a quantitative test to detect the presence of GAGs in urine through spectrophotometric methods using dimethylmethylene blue (DMB). The DMB test is based on the union of GAGs to the dimethylmethylene blue and the quantification of the GAG-DMB complex with a spectrophotometer. The sensitivity of this test is 100%, with a specificity of 75-100%. A negative result when detecting GAGs in urine does not rule out the existence of MPS III due to the fact that in some patients with attenuated forms of the disease, the levels of GAGs excretion with healthy controls can overlap and the increased excretion of heparan sulfate in the MPS III can be ignored. The current gold standard technique for diagnosis is the determination of enzyme activity in cultured skin fibroblasts, leukocytes, plasma or serum. The specific diagnosis of MPS IIIB is confirmed by showing a decrease or absence of one of the NAGLU enzymatic activities involved in the degradation of heparan sulfate in the patient's leukocytes or fibroblasts; the reduction should be less than 10% when compared to the activity in healthy individuals, with normalcy in other sulfatases. Because the disease due to deficiency in multiple sulfatases also shows a reduction in the activity of the heparan N-sulfatase, N-acetylglucosamine 6-sulfatase and other sulfatases, biochemical analysis of at least other sulfatase is required to confirm the diagnosis of MPS III and thus rule out multiple sulfatases deficiency. However, the method of diagnosis is not a limitation of the present invention and other suitable methods may be selected.

The method comprises administering to a subject a suspension of a vector as described herein. In one embodiment, the method comprises administering to a subject a suspension of a rAAV as described herein in a formulation buffer at a dose of about $1 \times 10^9$ GC per gram of brain mass to about $1 \times 10^{14}$ GC per gram of brain mass.

The composition(s) and method(s) provided achieve efficacy in treating a subject in need with MPS IIIB. Efficacy of the method in a subject can be shown by assessing (a) an increase in NAGLU enzymatic activity; (b) amelioration of a MPS IIIB symptom; (c) improvement of MPS IIIB-related biomarkers, e.g., GAG levels polyamine (e.g., spermine) levels in the cerebrospinal fluid (CSF), serum, urine and/or other biological samples; or (e) facilitation of any treatment(s) for MPS IIIB. In certain embodiments, efficacy may be determined by monitoring cognitive improvement and/or anxiety correction, gait and/or mobility improvement, reduction in tremor frequency and/or severity, reduction in clasping/spasms, improvements in posture, improvements in corneal opacity. Examples of suitable scoring, which is hereby incorporated in this section. Additionally or alternatively, efficacy of the method may be predicted based on an animal model. One example of a suitable murine model is described in Example 1. In another embodiment, a multiparameter grading scale (see, FIG. 5 incorporated herein by reference) was developed to evaluate disease correction and response to the MPSIIIA vector therapy described herein in an animal model. Animals are assigned a score based on an assessment of a combination of tremor, posture, fur quality, clasping, corneal clouding, and gait/mobility. In certain embodiments, any combination of one or more of these factors may be used to demonstrate efficacy, alone, or in combination with other factors. See, Burkholder et al. Curr Protoc Mouse Biol. June 2012, 2:145-65; Tumpey et al. J Virol. May 1998, 3705-10; and Guyenet et al. J Vis Exp, May 2010, 39; 1787). Cognitive improvement and anxiety correction of treated animals is evaluated by assessing movement in an open field (i.e. beam break measurement as described, e.g., in Tatem et al. J Vis Exp, 2014, (91):51785) and the elevated plus maze assay (as described, e.g., in Walf and Frye, Nat Protoc, 2007, 2(2): 322-328).

As used herein, "facilitation of any treatment(s) for MPS IIIB" or any grammatical variant thereof, refers to a decreased dosage or a lower frequency of a treatment of MPS IIIB in a subject other than the composition(s) or method(s) which is/are firstly disclosed in the invention, compared to that of a standard treatment without administration of the described composition(s) and use of the described method(s).

Examples of suitable treatment facilitated by the composition(s) or method(s) described herein might include, but not limited to, (a) medications used to relieve symptoms (such as seizures and sleep disturbances) and improve quality of life;

(b) hematopoietic stem cell transplantation, such as bone marrow transplantation or umbilical cord blood transplantation (see, e.g., Vellodi A, Young E, New M, Pot-Mees C, Hugh-Jones K. Bone marrow transplantation for Sanfilippo disease type B. J Inherit Metab Dis. 1992; 15: 911-8; Garbuzova-Davis, S, Willing, A E, Desjarlais, T, et al. Transplantation of human umbilical cord blood cells benefits an animal model of Sanfilippo syndrome type B. Stem Cells Dev. 2005; 14:384-394; and Garbuzova-Davis, S, Klasko, S K, and Sanberg, P R. Intravenous administration of human umbilical cord blood cells in an animal model of MPS III B. J Comp Neurol. 2009; 515:93-101.);

(c) enzyme replacement therapies (ERT) (e.g., via intravenous administration or intracerebroventricular infusion, see, e.g., Aoyagi-Scharber M et al, Clearance of Heparan Sulfate and Attenuation of CNS Pathology by Intracerebroventricular BMN 250 (NAGLU-IGF2) in Sanfilippo Type B Mice, Mol Ther Methods Clin Dev. 2017 Jun. 6; 6:43-53. doi: 10.1016/j.omtm.2017.05.009. eCollection 2017 Sep. 15; and Alexion Pharmaceuticals. Safety, Pharmacokinetics, and Pharmacodynamics/Efficacy of SBC-103 in MPS IIIB. In: ClinicalTrialsgov [Internet]. Bethesda: National Library of Medicine (US). 2000, Available from: clinicaltrials.gov/show/NCT02324049. NLM identifier: NCT02324049.);

(d) substrate reduction therapy (e.g., treatment with genistein. Delgadillo V et al. Genistein supplementation in patients affected by Sanfilippo disease. J Inherit Metab Dis. 2011 October; 34(5):1039-44. doi: 10.1007/s10545-011-9342-4. Epub 2011 May 10; Piotrowska E et al, Two-year follow-up of Sanfilippo Disease patients treated with a genistein-rich isoflavone extract: assessment of effects on cognitive functions and general status of patients. Med Sci Monit. 2011 April; 17(4): CR196-202; and Piotrowska, E et al, Genistin-rich soy isoflavone extract in substrate reduction therapy for sanfilippo syndrome: an openlabel, pilot study in 10 pediatric patients. Curr. Ther. Res. Clin. Exp. 2008; 69: 166-179);

(e) chaperone therapy (see, IGF2 in Kan S H, Troitskaya L A, Sinow C S, Haitz K, Todd A K, Di Stefano A, et al. Insulin-like growth factor II peptide fusion enables uptake and lysosomal delivery of alpha-N-acetylglucosaminidase to mucopolysaccharidosis type IIIB fibroblasts. Biochem J. 2014; 458:281-9; HIRMAb in Boado R J, Lu J Z, Hui E K, Lin H, Pardridge W M. Insulin Receptor Antibody alpha-N-Acetylglucosaminidase Fusion Protein Penetrates the Primate Blood-Brain Barrier and Reduces Glycosoaminoglycans in Sanfilippo Type B Fibroblasts. Mol Pharm. 2016; 13:1385-92; CpGH89 inhibitor in Ficko-Blean, E, Stubbs, K A, Nemirovsky, O, et al. Structural and mechanistic insight into the basis of mucopolysaccharidosis IIIB. Proc Natl Acad Sci USA. 2008; 105:6560-6565; and Zhao, K W and Neufeld, E F. Purification and characterization of recombinant human alpha-N-acetylglucosaminidase secreted by Chinese hamster ovary cells. Protein Expr Purif. 2000; 19:202-211); and (f) any combination thereof.

In one embodiment, the described method results in the subject demonstrating an improvement of biomarkers related to MPS IIIB.

An "increase in NAGLU enzymatic activity" is used interchangeably with the term "increase in desired NAGLU function", and refers to a NAGLU activity at least about 5%, 10%, 15%, 20%, about 25%, about 30%, about 35%, about 40%, about 45%, about 50%, about 55%, about 60%, about 65%, about 70%, about 75%, about 80%, about 85%, about 90%, about 95%, or about 100% of the NAGLU enzyme range for a healthy patient. The NAGLU enzymatic activity might be measured by an assay as described herein. In one embodiment, the NAGLU enzymatic activity might be measured in the serum, plasma, blood, urine, CSF, or another biological sample. In one embodiment, administration of the composition as described herein, or use of the method as described herein, result in an increase in NAGLU enzymatic activity in serum, plasma, saliva, urine or other biological samples. Alternatively, CSF GAG levels and other CSF biomarkers such as spermine levels may be measured to determine therapeutic effect. See. e.g., WO 2017/136533.

Neurocognition can be determined by conventional methods, See. e.g., WO 2017/136500 A1. Prevention of neurocognitive decline refers to a slowdown of a neurocognitive decline of the subject administered with the composition described herein or received the method described herein by at least about 5%, at least about 20%, at least about 20%, about 25%, about 30%, about 35%, about 40%, about 45%, about 50%, about 55%, about 60%, about 65%, about 70%, about 75%, about 80%, about 85%, about 90%, about 95%, or about 100% compared to that of a MPS IIIB patient.

As used herein, the terms "biomarker" or "MPS IIIB-related biomarker" refer to presence, concentration, expression level or activity of a biological or chemical molecular in a biological sample of a subject which correlates to progression or development of MPS IIIB in a positive or negative matter. In one embodiment, the biomarker is GAG levels in the cerebrospinal fluid (CSF), serum, urine, skin fibroblasts, leukocytes, plasma, or any other biological samples. In another embodiment, the biomarker is assessed using clinical chemistry. In yet another embodiment, the biomarker is liver or spleen volumes. In one embodiment, the biomarker is the activity of the heparan N-sulfatase, N-acetylglucosamine 6-sulfatase and other sulfatases. In another embodiment, the biomarker is spermine level in CSF, serum, or another biological sample. In yet another embodiment, the biomarker is lysosomal enzyme activity in serum, CSF, or another biological sample. In one embodiment, the biomarker is assessed via magnetic resonance imaging (MRI) of brain. In another embodiment, the biomarker is a neurocognitive score measured by a neurocognitive developmental test. The phrase "improvement of biomarker" as used herein means a reduction in a biomarker positively correlating to the progression of the disease, or an increase in a biomarker negatively correlating to the progression of the disease, wherein the reduction or increase is at least about 5%, at least about 20%, at least about 20%, about 25%, about 30%, about 35%, about 40%, about 45%, about 50%, about 55%, about 60%, about 65%, about 70%, about 75%, about 80%, about 85%, about 90%, about 95%, or about 100% compared to that before administration of the composition as described herein or use of the method as described herein.

In one embodiment, the method further comprises detecting or monitoring biomarkers related to MPS IIIB in the subject prior to initiation of therapy with therapy provided herein. In one aspect, the method comprises detection of a biomarker which is a polyamine (such as spermine) in a sample from a subject (see WO/2017/136533, which is incorporated herein by reference). Thus, in one embodiment, the method comprises detecting spermine in a patient sample for purposes of diagnosing a patient with MPSIIIB. In another embodiment, spermine concentration levels in a patient sample are detected to monitor the effectiveness of a treatment for MPSIIIB using the vector as described herein. Currently, patients with MPSIIIB are not considered candidates for bone marrow transplantation (BMT), Substrate Reduction Therapy (SRT) or enzyme replacement therapy (ERT). However, in certain embodiments, a gene therapy patient treated with a vector expressing the NAGLU described herein has, at a minimum, sufficient enzyme expression levels that any sub-normal range enzyme levels can be treated with ERT or SRT. Such ERT may be a co-therapy in which the dose of the ERT is monitored and modulated for months or years post-vector dosing. Additionally or alternatively, a SRT may be a co-therapy in which the dose of the SRT is monitored and modulated for months or years post-vector dosing. Additionally or alternatively, a chaperone therapy may be a co-therapy in which the dose of the chaperone therapy is monitored and modulated for months or years post-vector dosing.

Thus, in one embodiment, the suspension is suitable for co-administering with a functional hNAGLU protein or a recombinant protein comprising a functional NAGLU. In one embodiment, the recombinant protein is a NAGLU fused with insulin-like growth factor 2 (IGF2).

In one embodiment, the suspension is delivered into the subject in need intracerebroventricularly, intrathecally, intracisternaly or intravenously.

In one embodiment, the suspension has a pH of about 7.28 to about 7.32.

As used herein, an enzyme replacement therapy (ERT) is a medical treatment that consists in replacing an enzyme in patients where a particular enzyme is deficient or absent. The enzyme is usually produced as a recombinant protein and administrated to the patient. In one embodiment, the enzyme is a functional NAGLU. In another embodiment, the enzyme is a recombinant protein comprising a functional NAGLU. In one embodiment, the enzyme is a recombinant protein comprising a functional NAGLU and an insulin-like growth factor 2 (IGF2).Aoyagi-Scharber M et al, Clearance of Heparan Sulfate and Attenuation of CNS Pathology by Intracerebroventricular BMN 250 in Sanfilippo Type B Mice, Mol Ther Methods Clin Dev. 2017 Jun. 6; 6:43-53. doi: 10.1016/j.omtm.2017.05.009. eCollection 2017 Sep. 15; and WO2017132675A1. Systemic, intrathecal, intracerebroventricular or intracisternal delivery can be used for ERT or SRT co-therapy.

As used herein, an Substrate Reduction Therapy (SRT) refers to a therapy using a small molecule drug to partially inhibit the biosynthesis of the compounds, which accumulate in the absence of NAGLU. In one embodiment, the SRT is a therapy via genistein. See, e.g., Ritva Tikkanen et al, Less Is More: Substrate Reduction Therapy for Lysosomal Storage Disorders. Int J Mol Sci. 2016 July; 17(7): 1065. Published online 2016 Jul. 4. doi: 10.3390/ijms17071065; Delgadillo V et al, Epub 2011 May 10; and de Ruijter J et al, Genistein in Sanfilippo disease: a randomized controlled crossover trial. Ann Neurol. 2012 January; 71(1):110-20. doi: 10.1002/ana.22643. NAGLU.

As used herein, a chaperone therapy refers to a therapy using a small molecule drug to helps folding and/or secretion of NAGLUE. In one embodiment, the chaperone therapy is a therapy via IGF2. See, e.g., Kan S H, Troitskaya L A, Sinow C S, Haitz K, Todd A K, Di Stefano A, et al. Insulin-like growth factor II peptide fusion enables uptake and lysosomal delivery of alpha-N-acetylglucosaminidase to mucopolysaccharidosis type IIIB fibroblasts. Biochem J. 2014; 458:281-9; and HIRMAb in Boado R J, Lu J Z, Hui E K, Lin H, Pardridge WM. Insulin Receptor Antibody alpha-N-Acetylglucosaminidase Fusion Protein Penetrates the Primate Blood-Brain Barrier and Reduces Glycosoaminoglycans in Sanfilippo Type B Fibroblasts. Mol Pharm. 2016;13:1385-92. In another embodiment, the chaperone therapy is a therapy via CpGH89 inhibitor. See, e.g., Ficko-Blean, E, Stubbs, K A, Nemirovsky, O, et al. Structural and mechanistic insight into the basis of mucopolysaccharidosis IIIB. Proc Natl Acad Sci USA. 2008; 105:6560-6565. In yet another embodiment, the chaperone therapy is a therapy disclosed in Zhao, K W and Neufeld, E F. Purification and characterization of recombinant human alpha-N-acetylglucosaminidase secreted by Chinese hamster ovary cells. Protein Expr Purif. 2000; 19:202-211.

Suitable volumes for delivery of these doses and concentrations may be determined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

In one embodiment, the rAAV as described herein is administrable at a dose of about $1 \times 10^9$ GC per gram of brain mass to about $1 \times 10^{14}$ GC per gram of brain mass. In certain embodiments, the rAAV is co-administered systemically at a dose of about $1 \times 10^9$ GC per kg body weight to about $1 \times 10^{13}$ GC per kg body weight In one embodiment, the subject is delivered a therapeutically effective amount of the vectors described herein. As used herein, a "therapeutically effective amount" refers to the amount of the composition comprising the nucleic acid sequence encoding a functional NAGLU which delivers and expresses in the target cells an amount of enzyme sufficient to achieve efficacy. In one embodiment, the dosage of the vector is about $1 \times 10^9$ GC per gram of brain mass to about $1 \times 10^{13}$ genome copies (GC) per gram (g) of brain mass, including all integers or fractional amounts within the range and the endpoints. In another embodiment, the dosage is $1 \times 10^{10}$ GC per gram of brain mass to about $1 \times 10^{13}$ GC per gram of brain mass. In specific embodiments, the dose of the vector administered to a patient is at least about $1.0 \times 10^9$ GC/g, about $1.5 \times 10^9$ GC/g, about $2.0 \times 10^9$ GC/g, about $2.5 \times 10^9$ GC/g, about $3.0 \times 10^9$ GC/g, about $3.5 \times 10^9$ GC/g, about $4.0 \times 10^9$ GC/g, about $4.5 \times 10^9$ GC/g, about $5.0 \times 10^9$ GC/g, about $5.5 \times 10^9$ GC/g, about $6.0 \times 10^9$ GC/g, about $6.5 \times 10^9$ GC/g, about $7.0 \times 10^9$ GC/g, about $7.5 \times 10^9$ GC/g, about $8.0 \times 10^9$ GC/g, about $8.5 \times 10^9$ GC/g, about $9.0 \times 10^9$ GC/g, about $9.5 \times 10^9$ GC/g, about $1.0 \times 10^{10}$ GC/g, about $1.5 \times 10^{10}$ GC/g, about $2.0 \times 10^{10}$ GC/g, about $2.5 \times 10^{10}$ GC/g, about $3.0 \times 10^{10}$ GC/g, about $3.5 \times 10^{10}$ GC/g, about $4.0 \times 10^{10}$ GC/g, about $4.5 \times 10^{10}$ GC/g, about $5.0 \times 10^{10}$ GC/g, about $5.5 \times 10^{10}$ GC/g, about $6.0 \times 10^{10}$ GC/g, about $6.5 \times 10^{10}$ GC/g, about $7.0 \times 10^{10}$ GC/g, about $7.5 \times 10^{10}$ GC/g, about $8.0 \times 10^{10}$ GC/g, about $8.5 \times 10^{10}$ GC/g, about $9.0 \times 10^{10}$ GC/g, about $9.5 \times 10^{10}$ GC/g, about $1.0 \times 10^{11}$ GC/g, about $1.5 \times 10^{11}$ GC/g, about $2.0 \times 10^{11}$ GC/g, about $2.5 \times 10^{11}$ GC/g, about $3.0 \times 10^{11}$ GC/g, about $3.5 \times 10^{11}$ GC/g, about $4.0 \times 10^{11}$ GC/g, about $4.5 \times 10^{11}$ GC/g, about $5.0 \times 10^{11}$ GC/g, about $5.5 \times 10^{11}$ GC/g, about $6.0 \times 10^{11}$ GC/g, about $6.5 \times 10^{11}$ GC/g, about $7.0 \times 10^{11}$ GC/g, about $7.5 \times 10^{11}$ GC/g, about $8.0 \times 10^{11}$ GC/g, about $8.5 \times 10^{11}$ GC/g, about $9.0 \times 10^{11}$ GC/g, about $9.5 \times 10^{11}$ GC/g, about $1.0 \times 10^{12}$ GC/g, about $1.5 \times 10^{12}$ GC/g, about $2.0 \times 10^{12}$ GC/g, about $2.5 \times 10^{12}$ GC/g, about $3.0 \times 10^{12}$ GC/g, about $3.5 \times 10^{12}$ GC/g, about $4.0 \times 10^{12}$ GC/g, about $4.5 \times 10^{12}$ GC/g, about $5.0 \times 10^{12}$ GC/g, about $5.5 \times 10^{12}$ GC/g, about $6.0 \times 10^{12}$ GC/g, about $6.5 \times 10^{12}$ GC/g, about $7.0 \times 10^{12}$ GC/g, about $7.5 \times 10^{12}$ GC/g, about $8.0 \times 10^{12}$ GC/g, about $8.5 \times 10^{12}$ GC/g, about $9.0 \times 10^{12}$ GC/g, about $9.5 \times 10^{12}$ GC/g, about $1.0 \times 10^{13}$ GC/g, about $1.5 \times 10^{13}$ GC/g, about $2.0 \times 10^{13}$ GC/g, about $2.5 \times 10^{13}$ GC/g, about $3.0 \times 10^{13}$ GC/g, about $3.5 \times 10^{13}$ GC/g, about $4.0 \times 10^{13}$ GC/g, about $4.5 \times 10^{13}$ GC/g, about $5.0 \times 10^{13}$ GC/g, about $5.5 \times 10^{13}$ GC/g, about $6.0 \times 10^{13}$ GC/g, about $6.5 \times 10^{13}$ GC/g, about $7.0 \times 10^{13}$ GC/g, about $7.5 \times 10^{13}$ GC/g, about $8.0 \times 10^{13}$ GC/g, about $8.5 \times 10^{13}$ GC/g, about $9.0 \times 10^{13}$ GC/g, about $9.5 \times 10^{13}$ GC/g, or about $1.0 \times 10^{14}$ GC/g brain mass.

In one embodiment, the method further comprises the subject receives an immunosuppressive co-therapy Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an antimetabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent.

In certain embodiments, the immunosuppressive therapy may be started 0, 1, 2, 7, or more days prior to the gene therapy administration. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week (7 days), about 60 days, or longer, as needed. In certain embodiments, a tacrolimus-free regimen is selected.

In certain embodiment, the method comprises measurement of serum anti-hNAGLU antibodies. Suitable assays of measuring anti-hNAGLU antibody are available, See, e.g., Example 1.

In one embodiment, the rAAV as described herein is administrated once to the subject in need. In another embodiment, the rAAV is administrated more than once to the subject in need.

It should be understood that the compositions in the method described herein are intended to be applied to other compositions, regiments, aspects, embodiments and methods described across the Specification.

7. Kit

In certain embodiments, a kit is provided which includes a concentrated vector suspended in a formulation (optionally frozen), optional dilution buffer, and devices and components required for intrathecal, intracerebroventricular or intracisternal administration. In another embodiment, the kit may additional or alternatively include components for intravenous delivery. In one embodiment, the kit provides sufficient buffer to allow for injection. Such buffer may allow for about a 1:1 to a 1:5 dilution of the concentrated vector, or more. In other embodiments, higher or lower amounts of buffer or sterile water are included to allow for dose titration and other adjustments by the treating clinician. In still other embodiments, one or more components of the device are included in the kit. Suitable dilution buffer is available, such as, a saline, a phosphate buffered saline (PBS) or a glycerol/PBS.

It should be understood that the compositions in kit described herein are intended to be applied to other compositions, regiments, aspects, embodiments and methods described across the Specification.

8. Device

In one aspect, the vectors provided herein may be administered intrathecally via the method and/or the device described, e.g., in WO 2017/136500, which is incorporated herein by reference in its entirety. Alternatively, other devices and methods may be selected. In summary, the method comprises the steps of advancing a spinal needle into the cisterna magna of a patient, connecting a length of flexible tubing to a proximal hub of the spinal needle and an output port of a valve to a proximal end of the flexible tubing, and after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve. After connecting the first and second vessels to the valve, a path for fluid flow is opened between the vector inlet port and the outlet port of the valve and the pharmaceutical composition is injected into the patient through the spinal needle, and after injecting the pharmaceutical composition, a path for fluid flow is opened through the flush inlet port and the outlet port of the valve and the isotonic solution is injected into the spinal needle to flush the pharmaceutical composition into the patient. This method and this device may each optionally be used for intrathecal delivery of the compositions provided herein. Alternatively, other methods and devices may be used for such intrathecal delivery.

It should be understood that the compositions in the device described herein are intended to be applied to other compositions, regiments, aspects, embodiments and methods described across the Specification.

EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1: Methods

A. Vector-AAV9.CB7.C1. hNAGLUco.rBG

A hNAGLU codon-optimized sequence as shown in SEQ ID NO: 1 was cloned into an expression construct containing a CB7 promoter (a hybrid of a cytomegalovirus immediate-early enhancer and the chicken β-actin promoter), chicken β-actin intron (CI), and rabbit beta globin (rBG) polyadenylation sequence. The expression construct was flanked by AAV2 inverted terminal repeats and an AAV9 trans plasmid was used for encapsidation.

AAV vectors were manufactured by Penn Vector Core with iodixanol gradient method. See, Lock, M., et al., Rapid, Simple, and Versatile Manufacturing of Recombinant Adeno-Associated Viral Vectors at Scale. Human Gene Therapy, 2010. 21(10): p. 1259-1271. The purified vectors were titrated with classic qPCR for MPS IIIB by Penn Vector Core.

Dubelco's phosphate buffer saline (dPBS) without calcium and magnesium was used as control article (vehicle control) and diluent for vector. The test article was diluted with sterile phosphate buffered saline (PBS) to the appropriate concentration for each dose group. Diluted vector was kept on wet ice and injected to the animals within 4 hours after dilution.

B. Animal Procedures

All animal protocols were approved by the Institutional Animal Care and Use Committee of the University of Pennsylvania. NAGLU knock-out mice were maintained in the Gene Therapy Program vivarium at the University of Pennsylvania. All offspring were genotyped by PCR analysis of tail snip DNA using an automated system (Transnetyx Inc, 8110 Cordova Road Suite 119 Cordova, Tenn. 38016). Mice were grouped based on their genotype after weaning and were not mixed after that to prevent fighting; all animals in a given cage received the same treatment.

Animals were housed in standard caging of 1-5 animals/cage under 12-hour light/dark cycle controlled via automatic timer with a humidity of 30-70%. Temperature was kept within the range of 64-79° F. (18-26° C.). Autoclaved rodent chow food was provided ad libitum. Water was accessible to all animals ad libitum via individual placed water bottles in each cage. At a minimum, water bottles were replaced once per week during weekly cage changes. The water supply was drawn from the City of Philadelphia and purified using a Getinge water purifier. Water quality is tested by ULAR daily for chlorine levels and quarterly for pH and hardness.

Nesting material (Nestlet®) was provided in each cage after each change. Animals were monitored daily by GTP staff and ULAR veterinary staff.

C. Vector and Vehicle Administration

MPS IIIB mice vector doses were $3\times10^8$, $3\times10^9$ or $3\times10^{10}$ GC per mouse at an average age of 18 weeks. It is noted that ddPCR (Lock, M., et al., Absolute Determination of Single-Stranded and Self-Complementary Adeno-Associated Viral Vector Genome Titers by Droplet Digital PCR. Human Gene Therapy Methods, 2014. 25(2): p. 115-125) gives titers that are approximately 3 fold higher than the classic qPCR method. Mice were anesthetized with Isoflurane. Each anesthetized mouse was grasped firmly by the loose skin behind the head and injected free hand anterior and lateral to the bregma with a Hamilton syringe fitted with a 27-gauge needle, which was adjusted to be inserted 3 mm deep.

D. Neurobehavioral Assessment

Rocking rotarod was performed to assess coordination and balance 2 months pi (MPS IIIB). Mice were habituated to the rotarod during 2 trials at a constant low speed (5 rpm) for 120 seconds. After 2 minutes rest, mice were placed back on the rotarod and submitted to a rocking paradigm were the rod rotates at a constant speed of 10 rpm with reversal of the rotation direction every other rotation. 3 trials were performed with intertrial rest of 2 minutes. Results were expressed as the average latency to fall from the rod; the longer the latency, the better the coordination.

E. Histology

Mice were euthanized by cardiac puncture exsanguination under ketamine/xylazine anesthesia 3 months post injection. Tissues were promptly collected, half was snap-frozen on dry ice (enzyme activity), and half was immersion-fixed in 10% neutral formalin and embedded in paraffin for histology. Collected tissues were brain, spinal cord, liver, and heart.

Hematoxylin & eosin (H&E) staining was performed according to standard protocols on paraffin sections. Histopathology was scored in brain and spinal cord by a board-certified veterinary Pathologist blinded to the treatment. Brain score was the cumulative sum of 4-grade severity scores of glial cell vacuolation in brain, neuronal vacuolation in brain cortex, neuronal vacuolation in brainstem and hindbrain, perivascular mononuclear cell infiltration mononuclear cell infiltration (maximum score of 20). Cumulative scores were analyzed by one-way Anova Kruskall Wallis test with post hoc Dunn's multiple comparison test, alpha 0.05.

Lysosomal storage was assessed by LIMP2 immunostaining and quantification. LIMP2 immunostaining was performed on 6 µm sections from formalin-fixed paraffin-embedded brain tissue. Sections were deparaffinized through an ethanol and xylene series, boiled in a microwave for 6 minutes in 10 mmol/L citrate buffer (pH 6.0) for antigen retrieval, and blocked with 1% donkey serum in PBS+0.2% Triton for 15 minutes followed by sequential incubation with primary (1 hour) and labeled secondary (45 minutes) antibodies diluted in blocking buffer. The primary antibody was rabbit anti-LIMP2 (Novus Biologicals, Littleton, Colo., 1:200) and the secondary antibody was FITC- or TRITC-labeled donkey anti-rabbit (Jackson Immunoresearch). The number of cells staining positive for LIMP2 was quantified in 2-4 brain sections from each animal (Day 90 necropsies) by trained GTP Morphology core personnel.

F. Enzyme Activity and Glycosaminoglycan Storage

For enzyme activity assays and GAGs content, proteins were extracted by mechanical homogenization (Qiagen TissueLizer) in an acidic lysis solution (0.2% triton, 0.9% NaCl, adjusted to pH 4). Samples were freeze-thawed and clarified by centrifugation. Protein was quantified by BCA assay.

NAGLU activity was measured by incubating 10 µL sample with 20 µL of 2 mM 4-MU-2-Acetamido-2-deoxy-alpha-D-glucopyranoside (Toronto Research Chemicals) dissolved in sodium acetate 0.1M pH 3.58; NaCl 150 mM; Triton X100 0.05%. After incubating for 2 h at 37° C., the mixture was diluted in glycine NaOH buffer, pH 10.6, and released 4-MU was quantified by fluorescence (excitation 365 nm, emission 450 nm) compared with standard dilutions of free 4-MU and normalized by the protein content.

GAGs content in tissue extract is measured using dye-binding method with a commercial kit used per manufacturer recommendations (Blyscan Biocolor GAGs kit).

G. Anti-Transgene Antibodies

Blood for measurement of serum anti-hNAGLU antibodies was collected at several in vivo timepoints by submandibular bleeding as well as at terminal necropsy by cardiac puncture. Serum was separated and frozen on dry ice and stored at −80° C. until analyzed. Polystyrene plates were coated overnight with recombinant human NAGLU (R&D Systems), 5 µg/mL in PBS, titrated to pH 5.8. Plates were washed and blocked 1 hour in 2% bovine serum albumin (BSA) in neutral PBS. Plates were then incubated with serum samples diluted 1:1000 in PBS. Bound antibody was detected with horseradish peroxidase (HRP)-conjugated goat anti-mouse antibody (Abcam) diluted 1:10,000 in PBS with 2% BSA. The assay was developed using tetramethylbenzidine substrate and stopped with 2N sulfuric acid before measuring absorbance at 450 nm.

Example 2: Determination of Minimum Effective Dose (MED) in a Murine Model of MPSIIIb Experiments were performed to evaluate the expression, bioactivity, and minimum effective dose (MED) of a single intracerebroventricular (ICV) administration of AAV9.CB7.CI.hNAGLUco.rBG, an AAV9 vector expressing human N-acetyl-α-D-glucosaminidase (NAGLU), in a murine model of MPSIIIb.

AAV9.CB7.CI.hNAGLUco.rBG was administered through the ICV route to MPS IIIb mice, average age of 4 months (n=10 per group) at doses of $3\times10^8$ GC or $3\times10^9$ GC or $3\times10^{10}$ GC (determined by qPCR tittering of the vector) on Day 0 with a 3 month post-injection (pi) observation period. Vehicle treated MPS IIIb and heterozygous littermates served as controls (n=10 per group).

Bioactivity was assessed by measuring the NAGLU activity at 3 months pi in the brain, spinal cord, liver, serum and heart. Efficacy and MED were determined by measuring performance on a rocking rotarod at 2 months pi as well as brain and spinal cord lysosomal storage and histopathology at 3 month pi.

ICV administration of AAV9.CB7.CI.hNAGLUco.rBG to MPSIIIb mice at up to 3×10' GC was well tolerated, with no treatment related clinical signs or mortality, and resulted in NAGLU expression in the whole CNS (brain and spinal cord) as well as in peripheral tissues (liver, heart and serum).

Figure 2A:
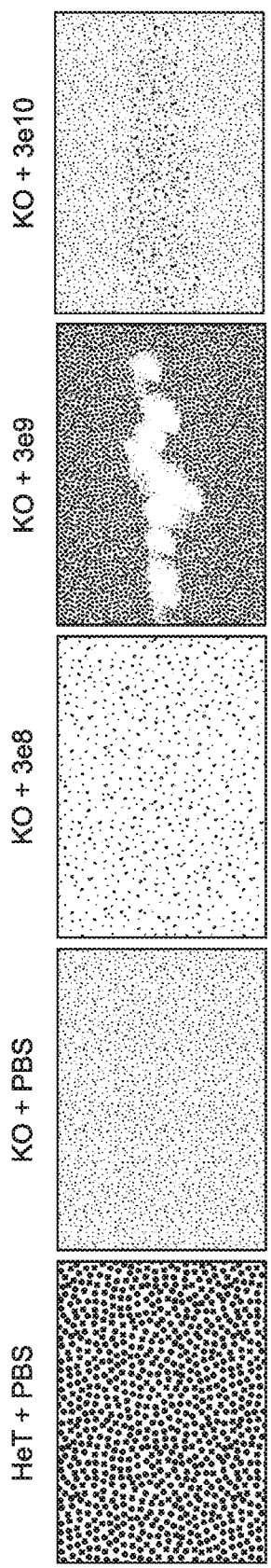
FIGS. 2A and 2B provide lysosomal storage assessed by LIMP2 immunostaining (FIG. 2A) and quantification (FIG. 2B) in brain 3 months after intracerebroventricular administration of AAV9.CB7.CI.hNAGLUco.rBG. LIMP2 immunostaining of lysosomal membranes show a reduction of the storage burden at the high dose (one way Anova Kruskall Wallis test with post hoc Dunn's multiple comparison test, alpha 0.05).
Figure 2B:
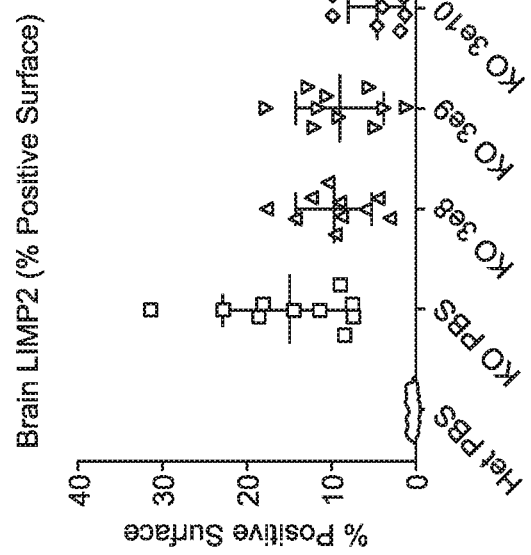
Figure 3A:
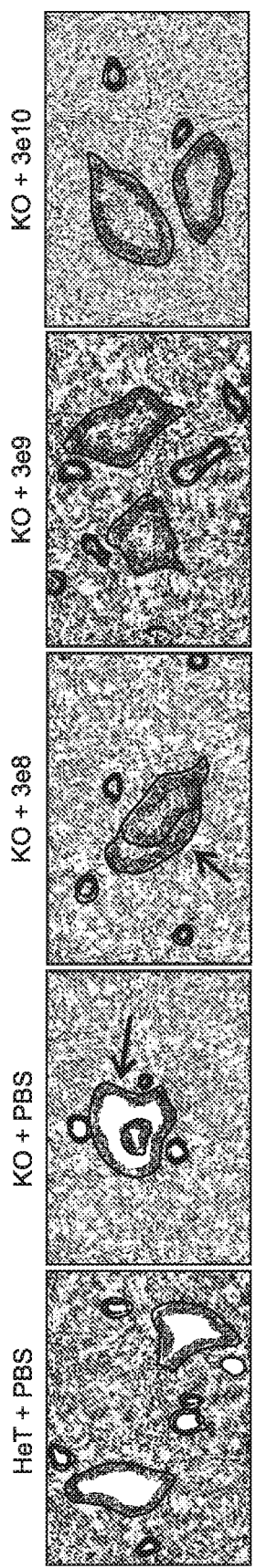
FIGS. 3A and 3B provide immunohistochemical staining (FIG. 3A) and histopathology cumulative score (FIG. 3B) in brain 3 months after ICV administration of AAV9.CB7.CI.hNAGLUco.rBG. Brain score is the cumulative sum of 4-grade severity scores of glial cell vacuolation in brain, neuronal vacuolation in brain cortex, neuronal vacuolation in brainstem and hindbrain, perivascular mononuclear cell infiltration mononuclear cell infiltration (maximum score of 20). Low dose MPS Mb mice are similar to vehicle-treated whereas both mid dose and high dose treated mice have a decreased neuropathology score in the brain and spinal cord (spinal cord not shown). The correction of neuropathology is statistically significant in the mid- and high dose groups treated animals (one way Anova Kruskall Wallis test with post hoc Dunn's multiple comparison test, alpha 0.05).
Figure 3B:
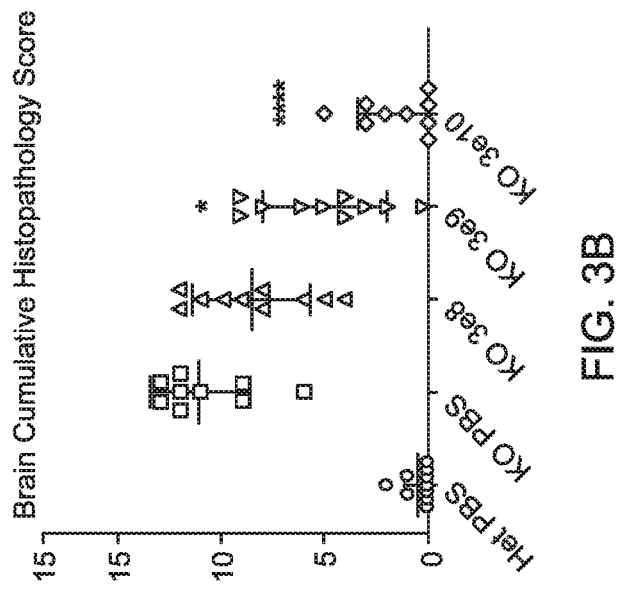
Figure 4:
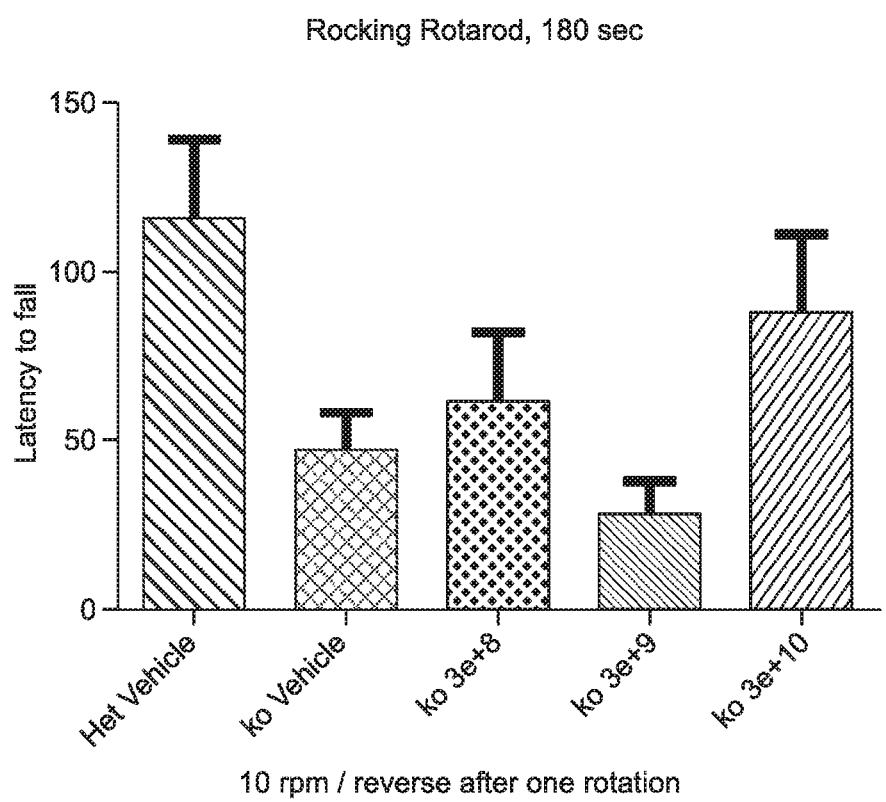
FIG. 4 shows neurologic function assessed by the rocking rotarod 2 months after ICV administration of AAV9.CB7.CI.hNAGLU.rBG. Mice are positioned on a rotating rod (10 revolutions per minutes) with an inversion of the rotation direction after each revolution. The latency to fall is measured over a maximum period of 180 seconds during 3 consecutive assays. The mean latency of the 3 assays is reported as an indicator of balance and coordination. Vehicle-treated MPS Mb mice present a neurologic deficit that cause them to fall from the rotating rod before heterozygous mice. High-dose treated mice tend to perform better than the untreated but statistical significance is not reached due to interindividual variability.

There were dose dependent increases in NAGLU activity in the brain, spinal cord, heart and liver at 3 month pi (FIG. 1) with enzymatic activity 50% of the heterozygous level at the mid dose in the brain and similar to or above the heterozygous level at high dose in all organs that were assessed. There was dose dependent normalization of the lysosomal compartment, as shown by reductions in LIMP2 staining in the brain at the high dose 3 months pi (FIGS. 2A and 2B). In H&E stained brain sections, dose dependent reductions in the amount and frequency of glial and neuronal vacuolation, indicators of lysosomal storage, were observed at the mid and high doses (FIGS. 3A and 3B). Neuronal storage and white matter axonopathy were corrected in the spinal cord at the high dose only (not shown). Corresponding to the changes in CNS lysosomal content and improvements in disease-related morphology in the H&E stained sections, there were improvement in the balance and coordination assessed by the rocking rotarod assay at 2 month pi at the high dose only, the statistical significance was however not reached due to interindividual variability (FIG. 4)

The test article and injection procedure were well tolerated. No clinical abnormality was noted in the mice apart from the MPs IIIb phenotype related signs. All mice survived up to the scheduled euthanasia. There was no evidence of test-article related toxicity in the brain on histopathology, although changes related to the ICV administration procedure itself were observed in some mice (focal hemosiderophages and mononuclear cell infiltrates in the periventricular parenchyma and meninges).

In conclusion, AAV9.CB7.CI.hNAGLUco.rBG was well tolerated in MPS IIIb mice at all dose levels and resulted in dose-dependent increases in NAGLU levels (expression and enzymatic activity) that were associated with improvements in both CNS and peripheral parameters of MPS IIIb with improvement of the neurobehavioral phenotype at the high dose. The high dose administered, $3\times10^{10}$ GC, was the minimum effective dose (MED) in this study (for neurobehavioral rescue) and the mid dose, $3\times10^{9}$ GC, was the MED if we consider enzymatic and pathology rescue of the brain. The treatment was administered relatively late (4 months) when the storage and neuroinflammation are already well developed, probably explaining the apparent lack of efficacy of the mid dose despite partial enzymatic rescue in the brain. The mid dose is anticipated to provide behavioral rescue if administered earlier.

Example 3: Pharmacology/Toxicology Study in Rhesus Macaque

Experiments are performed to evaluate the safety of intrathecal administration of three doses of AAV9.CB7.CI.hNAGLUco.rBG.

The control article is administered via suboccipital puncture to 3 macaques (both genders) in Group 1. The vector of AAV9.CB7.CI.hNAGLUco.rBG is administered via suboccipital puncture to 9 rhesus macaques randomized to Groups 2-4. Macaques in Group 3 receive test article high dose (N=3); macaques in Group 3 receive test article middle dose (N=3); macaques in Group 4 receive test article low dose (N=3). Blood and cerebrospinal fluid are collected as part of a general safety panel. Serum and peripheral blood mononuclear cells (PBMC) are collected to investigate humoral and cellular immune response to the capsid and transgene.

Following completion of the in-life phase of these studies at 90±3 days post-vector administration, macaques are necropsied with tissues harvested for a comprehensive histopathological examination. Lymphocytes are harvested from spleen, and bone marrow to examine the presence of CTLs in these organs at the time of necropsy.

Example 3: Long Term Effects of AAV.hNAGLU Administration

Experiments are performed to investigate the long-term effects of AAV.hNAGLU on MPS IIIb mice. Twenty MPS IIIb mice are injected with a high dose of AAV9.CB7.CI.hNAGLU.rBG ($9\times10^{10}$ GC, ICV) at 2 months of age. An additional twenty MPS IIIa mice and twenty wild-type mice receive PBS control injections. The mice are monitored for 7 months post injection, during which they are assigned clinical scores weekly and undergo behavioral and cognitive testing.

A multiparameter grading scale was developed to evaluate disease correction and response to treatment for the duration of the study. A score is assigned to individual mice based on an assessment of a combination of tremor, posture, fur quality, clasping, corneal clouding, and gait/mobility (FIG. 5). The clinical scoring system was adapted based on previously described methods (see, e.g., Burkholder et al. Curr Protoc Mouse Biol. June 2012, 2:145-65; Tumpey et al. J Virol. May 1998, 3705-10; and Guyenet et al. J Vis Exp, May 2010, 39; 1787).

Sequence Listing Free Text

The following information is provided for sequences containing free text under numeric identifier <223>.

| SEQ ID NO: (containing free text) | Free text under <223> |
|---|---|
| 1 | <223> Engineered nucleic acid sequence encoding human NAGLU protein |
| 4 | <223> rAAV vector genome AAV.CB7.CI.hNAGLUco.rBG<br><220><br><221> repeat_region<br><222> (1) ... (130)<br><223> 5' ITR<br><220><br><221> promoter<br><222> (198) ... (579)<br><223> CMV IE promoter<br><220><br><221> promoter<br><222> (582) ... (863)<br><223> CB promoter<br><220><br><221> TATA_signal<br><222> (836) ... (839)<br><220><br><221> Intron<br><222> (956) ... (1928)<br><223> chicken beta-actin intron<br><220><br><221> CDS<br><222> (1940) ... (4168)<br><223> Engineered nucleic acid sequence encoding human NAGLU protein<br><220><br><221> polyA_signal<br><222> (4235) ... (4361)<br><223> Rabbit globin polyA (rBG or RBG)<br><220><br><221> repeat_region<br><222> (4450) ... (4579)<br><223> 3' ITR |
| 5 | <223> Synthetic Construct |
| 6 | <223> capsid protein VP1 of adeno-associated virus 9 |
| 7 | <223> nucleic acid sequence encoding capsid protein VP1 of adeno-associated virus 9 |

All publications cited in this specification are incorporated herein by reference in their entireties as is U.S. Provisional Patent Application No. 62/593,090, filed Nov. 30, 2017. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant AAV (rAAV) comprising an AAV capsid and a vector genome packaged therein, wherein the vector genome comprises an AAV 5' inverted terminal repeat (ITR), an engineered nucleic acid sequence encoding a functional human N-acetyl-alpha-glucosaminidase (hNAGLU), a regulatory sequence which directs expression of hNAGLU in a target cell, and an AAV 3' ITR, wherein the hNAGLU coding sequence is at least 99% identical to SEQ ID NO: 1.

2. The rAAV according to claim 1, wherein the hNAGLU coding sequence is SEQ ID NO:1.

3. The rAAV according to claim 1, wherein the regulatory sequence comprises a promoter.

4. The rAAV according to claim 1 wherein the regulatory sequence further comprises an enhancer.

5. The rAAV according to claim 1, wherein the regulatory sequence further comprises an intron.

6. The rAAV according to claim 1, wherein the regulatory sequence further comprises a poly A.

7. The rAAV according to claim 1, wherein the AAV vector genome comprises the sequence of SEQ ID NO: 4.

8. The rAAV according to claim 1, wherein the AAV capsid is an AAV9 capsid.

9. The rAAV according to claim 1, which is for use in the treatment of Mucopolysaccharidosis III B (MPS IIIB) and/or improving gait or mobility, reducing tremors, reducing spasms, improving posture, or reducing the progression of vision loss in a subject in need thereof.

10. A pharmaceutical composition comprising a rAAV according to claim 1 in a formulation buffer.

11. The pharmaceutical composition according to claim 10, which is suitable for co-administering with a full-length functional hNAGLU protein.

12. The pharmaceutical composition according to claim 10, which is formulated for delivery via intracerebroventricular (ICV), intrathecal (IT), intracisternal or intravenous (IV) injection.

13. The pharmaceutical composition according to claim 10, which is administrable at a dose of $1\times10^9$ GC per gram of brain mass to about $1\times10^{13}$ GC per gram of brain mass.

14. The pharmaceutical composition according to claim 10, which is formulated to have a pH of 6 to 8.

15. A method of treating a human subject diagnosed with MPS IIIB and/or improving gait or mobility, reducing tremors, reducing spasms, improving posture, or reducing the progression of vision loss in a subject in need thereof, comprising administering to the subject a suspension of a rAAV according to claim 1 in a formulation buffer at a dose of $1\times10^9$ GC per gram of brain mass to about $1\times10^{13}$ GC per gram of brain mass.

16. The method according to claim 15, wherein said method results in a serum NAGLU activity at least about 20%, about 25%, about 30%, about 35%, about 40%, about 45%, about 50%, about 55%, about 60%, about 65%, about 70%, about 75%, about 80%, about 85%, about 90%, about 95%, or about 100% of a healthy control.

17. The method according to claim 15, wherein the suspension has at least $1\times10^{11}$ genome copy (GC)/mL of the rAAV.

18. The method according to claim 15, wherein the suspension is suitable for co-administering with a full-length hNAGLU protein.

19. The method according to claim 15, wherein the suspension is delivered into the subject intracerebroventricularly, intrathecally, or intravenously.

20. The method according to claim 15, wherein the suspension has a pH of 6 to 8.

21. The method according to claim 15, wherein
   (a) the subject receives an enzyme replacement therapy at a decreased dosage or with a lower frequency compared to a standard treatment via the enzyme replacement therapy only; and/or
   (b) IIIB, the subject demonstrates an improvement of biomarkers related to MPS.

22. The method according to claim 15, wherein the rAAV is administrated once to the subject in need.

23. The method according to claim 15, wherein the rAAV is administrated more than once to the subject in need.

24. A vector comprising an engineered nucleic acid sequence encoding a functional hNAGLU and a regulatory sequence which directs expression thereof in a target cell, wherein the hNAGLU coding sequence is at least 99% identical to SEQ ID NO: 1.

25. The vector according to claim 24, wherein the hNAGLU coding sequence is SEQ ID NO: 1.

26. The vector according to claim 24, which is a recombinant virus, a plasmid, Lipoplexes, a Polymersome, Polyplexes, a dendrimer, a cell penetrating peptide (CPP) conjugate, a magnetic particle, or a nanoparticle.

27. The vector according to claim 24, which is an adeno-associated virus (AAV), an adenovirus, a bocavirus, a hybrid AAV/bocavirus, a herpes simplex virus or a lentivirus.

28. The vector according to claim 24, wherein the target cell is an isolated cell, a cultured cell, a cell line, an *Escherichia coli* cell, a yeast cell, a human cell, a non-human cell, a mammalian cell, a non-mammalian cell, an insect cell, an HEK-293 cell, a liver cell, a kidney cell, a cell of the Central nervous system, a neuron, a glial cell, or a stem cell.

* * * * *

```
                           SEQUENCE LISTING

<160> NUMBER OF SEQ ID NOS: 7

<210> SEQ ID NO 1
<211> LENGTH: 2232
<212> TYPE: DNA
<213> ORGANISM: Artificial Sequence
<220> FEATURE:
<223> OTHER INFORMATION: Engineered nucleic acid sequence encoding human
      NAGLU protein

<400> SEQUENCE: 1
atggaagccg tggccgtggc tgctgctgtg ggagtgctgc tgctggctgg cgctggcgga      60
gctgctgggg atgaagctag agaagctgcc gctgtgcggg ccctggtggc tagactgctg     120
ggacctggac ctgccgccga tttcagcgtg tccgtggaaa gagccctggc cgccaagcct     180
ggcctggata cctattctct gggcggaggc ggagccgcca gagtcagagt gcggggatct     240
acaggcgtgg ccgctgcagc tggactgcac agatacctga gagacttctg cggctgccat     300
gtggcttgga gcggcagcca gctgagactg cctagacctc tgcctgccgt gcctggcgaa     360
ctgacagagg ccaccccaa cagataccgg tactaccaga acgtgtgcac ccagagctac     420
agcttcgtgt ggtgggactg ggccagatgg gagcgcgaga tcgattggat ggccctgaac     480
ggcatcaacc tggccctggc ttggagtggc caggaagcca tctggcagag agtgtacctg     540
gctctgggcc tgacccaggc cgagatcaac gagttcttta ccggccctgc ctttctggcc     600
tggggcagaa tgggcaacct gcacacatgg gacggccccc tgcctcctag ctggcacatc     660
aagcagctgt acctgcagca cagagtgctg gaccagatgg gtccttcgg catgacccct      720 gtgctgcctg cctttgccgg acatgtgcct gaggccgtga ccagagtgtt cccccaagtg     780
aacgtgacca gatgggcag ctggggccac ttcaactgca gctactcctg cagcttcctg      840
ctggcccccg aggacccat cttccctatt atcggcagcc tgttcctgcg cgagctgatc      900
aaagagttcg gcaccgacca catctacggc gccgacacct caacgagat gcagcccct      960 agcagcgagc ccagctatct ggccgcagcc acaacagccg tgtacgaggc catgaccgcc    1020
gtggatacag aggccgtgtg gctgctgcag ggctggctgt tcagcacca gccccagttt    1080 tggggccctg cccagattag agccgtgctg ggagctgtgc ccagaggcag gctgctggtg    1140
ctggatctgt ttgccgagag ccagcccgtg tacaccagaa ccgccagctt ccagggacag    1200
cccttcatct ggtgtatgct gcacaacttc ggcggcaacc acggcctgtt tggcgctctg    1260
gaagcagtga atgcggccc tgaagccgcc aggctgttcc ccaatagcac aatggtggga    1320
accggcatgg ccccagaggg catcagccag aacgaggtgg tgtacagcct gatggccgag    1380
ctgggatggc ggaaggaccc tgtgcctgat ctggctgcct gggtcaccag cttcgccgct    1440
agaagatacg gcgtgtccca ccctgatgcc ggcgctgctt ggcgcctgct gctgagaagc    1500
gtgtacaact gtagcggcga ggcctgcagg ggccacaata gatctccact cgtgcggagg    1560
cccagcctgc agatgaacac cagcatctgg tacaaccgca cgacgtgtt cgaggcttgg    1620 agactgctgc tgaccagcgc cccatctctg gccacaagcc ccgccttcag atacgacctg    1680
ctggacctga caaggcagcc cgtgcaggaa ctggtgtccc tgtactacga ggaagccaga    1740
agcgcctacc tgacaaaga gctggcctcc ctgctgagag caggcggcgt gctggcttat    1800
gaactgctgc ccgccctgga tgaggtgctg gcctctgact ccagatttct gctgggctcc    1860
```

```
tggctggaac aggccagagc agccgctgtg tctgaagccg aggccgactt ctacgagcag    1920
aacagcagat accagctgac cctgtgggga cccgagggca acatcctgga ctacgccaac    1980
aaacagctgg ccggcctggt ggccaactac tacacaccta gatggcggct gtttctggaa    2040
gctctggtgg actctgtggc ccagggcatc ccattccagc agcaccagtt cgacaagaac    2100
gtgttccagc tggaacaggc tttcgtgctg agcaagcaga gatacccctc ccagcccagg    2160
ggcgacacag tggatctggc caagaagatc tttctgaagt actaccccag atgggtggcc    2220
ggctcttggt ga                                                        2232
```

<210> SEQ ID NO 2
<211> LENGTH: 743
<212> TYPE: PRT
<213> ORGANISM: Homo sapiens

<400> SEQUENCE: 2

```
Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
    50                  55                  60

Tyr Ser Leu Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300
```

```
Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Thr Ala Val Tyr Glu
            325                 330                 335

Ala Met Thr Ala Val Asp Thr Glu Ala Val Trp Leu Leu Gln Gly Trp
                340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605

Val Leu Ala Ser Asp Ser Arg Phe Leu Leu Gly Ser Trp Leu Glu Gln
610                 615                 620

Ala Arg Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
            645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
            675                 680                 685

Gly Ile Pro Phe Gln Gln His Gln Phe Asp Lys Asn Val Phe Gln Leu
            690                 695                 700

Glu Gln Ala Phe Val Leu Ser Lys Gln Arg Tyr Pro Ser Gln Pro Arg
705                 710                 715                 720
```

```
Gly Asp Thr Val Asp Leu Ala Lys Lys Ile Phe Leu Lys Tyr Tyr Pro
            725                 730                 735

Arg Trp Val Ala Gly Ser Trp
        740

<210> SEQ ID NO 3
<211> LENGTH: 2232
<212> TYPE: DNA
<213> ORGANISM: Homo sapiens

<400> SEQUENCE: 3
atggaggcgg tggcggtggc cgcggcggtg ggggtccttc tcctggccgg ggccggggcc      60
gcggcaggcg acgaggcccg ggaggcggcg gccgtgcggg cgctcgtggc ccggctgctg     120
gggccaggcc ccgcggccga cttctccgtg tcggtggagc gcgctctggc tgccaagccg     180
ggcttggaca cctacagcct gggcggcggc ggcgcggcgc gcgtgcgggt gcgcggctcc     240
acgggcgtgg cggccgccgc ggggctgcac cgctacctgc gcgacttctg tggctgccac     300
gtggcctggt ccggctctca gctgcgcctg ccgcggccac tgccagccgt gccggggag     360 ctgaccgagg ccacgcccaa caggtaccgc tattaccaga atgtgtgcac gcaaagctac     420
tctttcgtgt ggtgggactg ggcccgctgg gagcgagaga tagactggat ggcgctgaat     480
ggcatcaacc tggcactggc ctggagcggc caggaggcca tctggcagcg ggtgtacctg     540
gccttgggcc tgacccaggc agagatcaat gagttcttta ctggtcctgc cttcctggcc     600
tgggggcgaa tggcaacct gcacacctgg gatggccccc tgcccccctc ctggcacatc     660
aagcagcttt acctgcagca ccgggtcctg gaccagatgc gctccttcgg catgaccca     720 gtgctgcctg cattcgcggg gcatgttccc gaggctgtca ccagggtgtt ccctcaggtc     780
aatgtcacga gatgggcag ttggggccac tttaactgtt cctactcctg ctccttcctt     840
ctggctccgg aagaccccat attccccatc atcgggagcc tcttcctgcg agagctgatc     900
aaagagtttg gcacagacca catctatggg ccgacacttt caatgagat gcagccacct     960 tcctcagagc cctcctacct tgccgcagcc accactgccg tctatgaggc catgactgca    1020
gtggatactg aggctgtgtg gctgctccaa ggctggctct ccagcacca gccgcagttc    1080 tgggggcccg cccagatcag ggctgtgctg ggagctgtgc ccgtggccg cctcctggtt    1140 ctggacctgt ttgctgagag ccagcctgt tatacccgca ctgcctcctt ccagggccag    1200 ccttcatct ggtgcatgct gcacaacttt ggggaaacc atggtctttt tggagcccta    1260
gaggctgtga acgaggccc agaagctgcc cgcctcttcc ccaactccac catggtaggc    1320
acgggcatgg cccccgaggg catcagccag aacgaagtgg tctattccct catggctgag    1380
ctgggctggc gaaaggaccc cagtgccaga ttggcagcct gggtgaccag cttttgccgcc    1440 cggcggtatg gggtctccca cccggacgca ggggcagcgt ggaggctact gctccggagt    1500
gtgtacaact gctccgggga ggcctgcagg ggccacaatc gtagcccgct ggtcaggcgg    1560
ccgtccctac agatgaatac cagcatctgg tacaaccgat ctgatgtgtt tgaggcctgg    1620
cggctgctgc tcacatctgc tccctccctg gccaccagcc ccgccttccg ctacgacctg    1680
ctggacctca ctcggcaggc agtgcaggag ctggtcagct tgtactatga ggaggcaaga    1740
agcgcctacc tgagcaagga gctggcctcc ctgttgaggg ctggaggcgt cctggcctat    1800
gagctgctgc cggcactgga cgaggtgctg ctagtgaca gccgcttctt gctgggcagc    1860
tggctagagc aggcccgagc agcggcagtc agtgaggccg aggccgattt ctacgagcag    1920
aacagccgct accagctgac cttgtggggg ccagaaggca acatcctgga ctatgccaac    1980
```

-continued

```
aagcagctgg cggggttggt ggccaactac tacacccctc gctggcggct tttcctggag    2040
gcgctggttg acagtgtggc ccagggcatc cctttccaac agcaccagtt tgacaaaaat    2100
gtcttccaac tggagcaggc cttcgttctc agcaagcaga ggtacgccag ccagccgcga    2160
ggagacactg tggacctggc caagaagatc ttcctcaaat attaccccg ctgggtggcc     2220 ggctcttggt ga                                                        2232
```

<210> SEQ ID NO 4
<211> LENGTH: 4579
<212> TYPE: DNA
<213> ORGANISM: Artificial Sequence
<220> FEATURE:
<223> OTHER INFORMATION: rAAV vector genome AAV.CB7.CI.hNAGLUco.rBG
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: CDS
<222> LOCATION: (1940)..(4168)
<223> OTHER INFORMATION: Engineered nucleic acid sequence encoding human
    NAGLU protein
<220> FEATURE:
<221> NAME/KEY: polyA_signal
<222> LOCATION: (4235)..(4361)
<223> OTHER INFORMATION: Rabbit globin polyA (rBG or RBG)
<220> FEATURE:
<221> NAME/KEY: repeat_region
<222> LOCATION: (4450)..(4579)
<223> OTHER INFORMATION: 3' ITR

<400> SEQUENCE: 4

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
agggattcct tgtagttaat gattaacccg ccatgctact tatctaccag ggtaatgggg    180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctccccccc ctccccaccc ccaatttgt atttatttat     660 tttttaatta ttttgtgcag cgatggggc ggggggggg gggggcgcg cgccaggcgg      720 ggcggggcgg ggcgaggggc ggggcgggc gaggcggaga ggtgcggcgg cagccaatca    780
```

-continued

```
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020 ttctttctg tggctgcgtg aaagccttga ggggctccgg gagggccctt tgtgcggggg    1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc gggggggggct gcgaggggaa   1260 caaaggctgc gtgcggggtg tgtgcgtggg ggggtgagca ggggtgtgg gcgcgtcggt    1320 cgggctgcaa ccccccctgc acccccctcc ccgagttgct gagcacggcc cggcttcggg   1380
tgcggggctc cgtacggggc gtggcgcggg gctcgccgtg ccgggcgggg ggtggcggca   1440
ggtgggggtg ccgggcgggg cggggccgcc tcgggccggg gagggctcgg ggaggggcg    1500 cggcggcccc cggagcgccg gcggctgtcg aggcgcggca agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cgggggggac ggggcagggc   1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgccacc atg gaa gcc gtg gcc gtg gct gct gct gtg gga   1972
                      Met Glu Ala Val Ala Val Ala Ala Ala Val Gly
                        1               5                      10 gtg ctg ctg ctg gct ggc gct ggc gga gct gct ggg gat gaa gct aga   2020
Val Leu Leu Leu Ala Gly Ala Gly Gly Ala Ala Gly Asp Glu Ala Arg
             15                  20                  25 gaa gct gcc gct gtg cgg gcc ctg gtg gct aga ctg ctg gga cct gga   2068
Glu Ala Ala Ala Val Arg Ala Leu Val Ala Arg Leu Leu Gly Pro Gly
         30                  35                  40 cct gcc gcc gat ttc agc gtg tcc gtg gaa aga gcc ctg gcc gcc aag   2116
Pro Ala Ala Asp Phe Ser Val Ser Val Glu Arg Ala Leu Ala Ala Lys
 45                  50                  55 cct ggc ctg gat acc tat tct ctg ggc gga ggc gga gcc gcc aga gtc   2164
Pro Gly Leu Asp Thr Tyr Ser Leu Gly Gly Gly Gly Ala Ala Arg Val
 60              65                  70                  75 aga gtg cgg gga tct aca ggc gtg gcc gct gca gct gga ctg cac aga   2212
Arg Val Arg Gly Ser Thr Gly Val Ala Ala Ala Ala Gly Leu His Arg
                 80                  85                  90 tac ctg aga gac ttc tgc ggc tgc cat gtg gct tgg agc ggc agc cag   2260
Tyr Leu Arg Asp Phe Cys Gly Cys His Val Ala Trp Ser Gly Ser Gln
             95                  100                 105 ctg aga ctg cct aga cct ctg cct gcc gtg cct ggc gaa ctg aca gag   2308
Leu Arg Leu Pro Arg Pro Leu Pro Ala Val Pro Gly Glu Leu Thr Glu
         110                 115                 120 gcc acc ccc aac aga tac cgg tac tac cag aac gtg tgc acc cag agc   2356
Ala Thr Pro Asn Arg Tyr Arg Tyr Tyr Gln Asn Val Cys Thr Gln Ser
 125                 130                 135 tac agc ttc gtg tgg tgg gac tgg gcc aga tgg gag cgc gag atc gat   2404
Tyr Ser Phe Val Trp Trp Asp Trp Ala Arg Trp Glu Arg Glu Ile Asp
 140                 145                 150                 155 tgg atg gcc ctg aac ggc atc aac ctg gcc ctg gct tgg agt ggc cag   2452
Trp Met Ala Leu Asn Gly Ile Asn Leu Ala Leu Ala Trp Ser Gly Gln
```

```
Trp Met Ala Leu Asn Gly Ile Asn Leu Ala Leu Ala Trp Ser Gly Gln
            160                 165                 170 gaa gcc atc tgg cag aga gtg tac ctg gct ctg ggc ctg acc cag gcc      2500
Glu Ala Ile Trp Gln Arg Val Tyr Leu Ala Leu Gly Leu Thr Gln Ala
        175                 180                 185 gag atc aac gag ttc ttt acc ggc cct gcc ttt ctg gcc tgg ggc aga      2548
Glu Ile Asn Glu Phe Phe Thr Gly Pro Ala Phe Leu Ala Trp Gly Arg
    190                 195                 200 atg ggc aac ctg cac aca tgg gac ggc ccc ctg cct cct agc tgg cac      2596
Met Gly Asn Leu His Thr Trp Asp Gly Pro Leu Pro Pro Ser Trp His
205                 210                 215 atc aag cag ctg tac ctg cag cac aga gtg ctg gac cag atg cgg tcc      2644
Ile Lys Gln Leu Tyr Leu Gln His Arg Val Leu Asp Gln Met Arg Ser
220                 225                 230                 235 ttc ggc atg acc cct gtg ctg cct gcc ttt gcc gga cat gtg cct gag      2692
Phe Gly Met Thr Pro Val Leu Pro Ala Phe Ala Gly His Val Pro Glu
        240                 245                 250 gcc gtg acc aga gtg ttc ccc caa gtg aac gtg acc aag atg ggc agc      2740
Ala Val Thr Arg Val Phe Pro Gln Val Asn Val Thr Lys Met Gly Ser
        255                 260                 265 tgg ggc cac ttc aac tgc agc tac tcc tgc agc ttc ctg ctg gcc ccc      2788
Trp Gly His Phe Asn Cys Ser Tyr Ser Cys Ser Phe Leu Leu Ala Pro
    270                 275                 280 gag gac ccc atc ttc cct att atc ggc agc ctg ttc ctg cgc gag ctg      2836
Glu Asp Pro Ile Phe Pro Ile Ile Gly Ser Leu Phe Leu Arg Glu Leu
285                 290                 295 atc aaa gag ttc ggc acc gac cac atc tac ggc gcc gac acc ttc aac      2884
Ile Lys Glu Phe Gly Thr Asp His Ile Tyr Gly Ala Asp Thr Phe Asn
300                 305                 310                 315 gag atg cag ccc cct agc agc gag ccc agc tat ctg gcc gca gcc aca      2932
Glu Met Gln Pro Pro Ser Ser Glu Pro Ser Tyr Leu Ala Ala Ala Thr
        320                 325                 330 aca gcc gtg tac gag gcc atg acc gcc gtg gat aca gag gcc gtg tgg      2980
Thr Ala Val Tyr Glu Ala Met Thr Ala Val Asp Thr Glu Ala Val Trp
        335                 340                 345 ctg ctg cag ggc tgg ctg ttt cag cac cag ccc cag ttt tgg ggc cct      3028
Leu Leu Gln Gly Trp Leu Phe Gln His Gln Pro Gln Phe Trp Gly Pro
    350                 355                 360 gcc cag att aga gcc gtg ctg gga gct gtg ccc aga ggc agg ctg ctg      3076
Ala Gln Ile Arg Ala Val Leu Gly Ala Val Pro Arg Gly Arg Leu Leu
365                 370                 375 gtg ctg gat ctg ttt gcc gag agc cag ccc gtg tac acc aga acc gcc      3124
Val Leu Asp Leu Phe Ala Glu Ser Gln Pro Val Tyr Thr Arg Thr Ala
380                 385                 390                 395 agc ttc cag gga cag ccc ttc atc tgg tgt atg ctg cac aac ttc ggc      3172
Ser Phe Gln Gly Gln Pro Phe Ile Trp Cys Met Leu His Asn Phe Gly
        400                 405                 410 ggc aac cac ggc ctg ttt ggc gct ctg gaa gca gtg aat ggc ggc cct      3220
Gly Asn His Gly Leu Phe Gly Ala Leu Glu Ala Val Asn Gly Gly Pro
        415                 420                 425 gaa gcc gcc agg ctg ttc ccc aat agc aca atg gtg gga acc ggc atg      3268
Glu Ala Ala Arg Leu Phe Pro Asn Ser Thr Met Val Gly Thr Gly Met
        430                 435                 440 gcc cca gag ggc atc agc cag aac gag gtg gtg tac agc ctg atg gcc      3316
Ala Pro Glu Gly Ile Ser Gln Asn Glu Val Val Tyr Ser Leu Met Ala
445                 450                 455 gag ctg gga tgg cgg aag gac cct gtg cct gat ctg gct gcc tgg gtc      3364
Glu Leu Gly Trp Arg Lys Asp Pro Val Pro Asp Leu Ala Ala Trp Val
460                 465                 470                 475
```

-continued

| | |
|---|---|
| acc agc ttc gcc gct aga aga tac ggc gtg tcc cac cct gat gcc ggc<br>Thr Ser Phe Ala Ala Arg Arg Tyr Gly Val Ser His Pro Asp Ala Gly<br>480            485            490 | 3412 |
| gct gct tgg cgc ctg ctg ctg aga agc gtg tac aac tgt agc ggc gag<br>Ala Ala Trp Arg Leu Leu Leu Arg Ser Val Tyr Asn Cys Ser Gly Glu<br>    495            500            505 | 3460 |
| gcc tgc agg ggc cac aat aga tct cca ctc gtg cgg agg ccc agc ctg<br>Ala Cys Arg Gly His Asn Arg Ser Pro Leu Val Arg Arg Pro Ser Leu<br>510            515            520 | 3508 |
| cag atg aac acc agc atc tgg tac aac cgc agc gac gtg ttc gag gct<br>Gln Met Asn Thr Ser Ile Trp Tyr Asn Arg Ser Asp Val Phe Glu Ala<br>525            530            535 | 3556 |
| tgg aga ctg ctg ctg acc agc gcc cca tct ctg gcc aca agc ccc gcc<br>Trp Arg Leu Leu Leu Thr Ser Ala Pro Ser Leu Ala Thr Ser Pro Ala<br>540            545            550            555 | 3604 |
| ttc aga tac gac ctg ctg gac ctg aca agg cag gcc gtg cag gaa ctg<br>Phe Arg Tyr Asp Leu Leu Asp Leu Thr Arg Gln Ala Val Gln Glu Leu<br>            560            565            570 | 3652 |
| gtg tcc ctg tac tac gag gaa gcc aga agc gcc tac ctg agc aaa gag<br>Val Ser Leu Tyr Tyr Glu Glu Ala Arg Ser Ala Tyr Leu Ser Lys Glu<br>        575            580            585 | 3700 |
| ctg gcc tcc ctg ctg aga gca ggc ggc gtg ctg gct tat gaa ctg ctg<br>Leu Ala Ser Leu Leu Arg Ala Gly Gly Val Leu Ala Tyr Glu Leu Leu<br>    590            595            600 | 3748 |
| ccc gcc ctg gat gag gtg ctg gcc tct gac tcc aga ttt ctg ctg ggc<br>Pro Ala Leu Asp Glu Val Leu Ala Ser Asp Ser Arg Phe Leu Leu Gly<br>605            610            615 | 3796 |
| tcc tgg ctg gaa cag gcc aga gca gcc gct gtg tct gaa gcc gag gcc<br>Ser Trp Leu Glu Gln Ala Arg Ala Ala Ala Val Ser Glu Ala Glu Ala<br>620            625            630            635 | 3844 |
| gac ttc tac gag cag aac agc aga tac cag ctg acc ctg tgg gga ccc<br>Asp Phe Tyr Glu Gln Asn Ser Arg Tyr Gln Leu Thr Leu Trp Gly Pro<br>            640            645            650 | 3892 |
| gag ggc aac atc ctg gac tac gcc aac aaa cag ctg gcc ggc ctg gtg<br>Glu Gly Asn Ile Leu Asp Tyr Ala Asn Lys Gln Leu Ala Gly Leu Val<br>        655            660            665 | 3940 |
| gcc aac tac tac aca cct aga tgg cgg ctg ttt ctg gaa gct ctg gtg<br>Ala Asn Tyr Tyr Thr Pro Arg Trp Arg Leu Phe Leu Glu Ala Leu Val<br>    670            675            680 | 3988 |
| gac tct gtg gcc cag ggc atc cca ttc cag cag cac cag ttc gac aag<br>Asp Ser Val Ala Gln Gly Ile Pro Phe Gln Gln His Gln Phe Asp Lys<br>685            690            695 | 4036 |
| aac gtg ttc cag ctg gaa cag gct ttc gtg ctg agc aag cag aga tac<br>Asn Val Phe Gln Leu Glu Gln Ala Phe Val Leu Ser Lys Gln Arg Tyr<br>700            705            710            715 | 4084 |
| ccc tcc cag ccc agg ggc gac aca gtg gat ctg gcc aag aag atc ttt<br>Pro Ser Gln Pro Arg Gly Asp Thr Val Asp Leu Ala Lys Lys Ile Phe<br>            720            725            730 | 4132 |
| ctg aag tac tac ccc aga tgg gtg gcc ggc tct tgg tgataaggta<br>Leu Lys Tyr Tyr Pro Arg Trp Val Ala Gly Ser Trp<br>        735            740 | 4178 |
| cctctagagt cgacccgggc ggcctcgagg acggggtgaa ctacgcctga ggatccgatc | 4238 |
| ttttccctc tgccaaaaat tatggggaca tcatgaagcc ccttgagcat ctgacttctg | 4298 |
| gctaataaag gaaatttatt tcattgcaa tagtgtgttg gaatttttg tgtctctcac | 4358 |
| tcggaagcaa ttcgttgatc tgaatttcga ccacccataa tacccattac cctggtagat | 4418 |
| aagtagcatg gcgggttaat cattaactac aaggaacccc tagtgatgga gttggccact | 4478 |
| ccctctctgc gcgctcgctc gctcactgag gccgggcgac caaaggtcgc ccgacgcccg | 4538 | ggctttgccc gggcggcctc agtgagcgag cgagcgcgca g    4579

<210> SEQ ID NO 5
<211> LENGTH: 743
<212> TYPE: PRT
<213> ORGANISM: Artificial Sequence
<220> FEATURE:
<223> OTHER INFORMATION: Synthetic Construct

<400> SEQUENCE: 5

```
Met Glu Ala Val Ala Val Ala Ala Val Gly Val Leu Leu Leu Ala
1               5                   10                  15

Gly Ala Gly Ala Ala Gly Asp Glu Ala Arg Glu Ala Ala Val
            20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
        50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
            340                 345                 350
```

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
        370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
            740

<210> SEQ ID NO 6
<211> LENGTH: 736
<212> TYPE: PRT

<213> ORGANISM: Artificial Sequence
<220> FEATURE:
<223> OTHER INFORMATION: capsid protein VP1 of adeno-associated virus 9

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

|   |   |   | 385 |   |   |   | 390 |   |   |   | 395 |   |   |   | 400 |
|---|---|---|---|---|---|---|---|---|---|---|---|---|---|---|---|

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 7
<211> LENGTH: 2211
<212> TYPE: DNA
<213> ORGANISM: Artificial Sequence
<220> FEATURE:
<223> OTHER INFORMATION: nucleic acid sequence encoding capsid protein
      VP1 of adeno-associated virus 9

<400> SEQUENCE: 7
atggctgccg atggttatct tccagattgg ctcgaggaca accttagtga aggaattcgc     60
gagtggtggg ctttgaaacc tggagcccct caacccaagg caaatcaaca acatcaagac    120

```
aacgctcgag gtcttgtgct tccgggttac aaataccttg gacccggcaa cggactcgac      180
aagggggagc cggtcaacgc agcagacgcg gcggccctcg agcacgacaa ggcctacgac      240
cagcagctca aggccggaga caacccgtac ctcaagtaca accacgccga cgccgagttc      300
caggagcggt caaagaaga tacgtctttt gggggcaacc tcgggcgagc agtcttccag       360
gccaaaaaga ggcttcttga acctcttggt ctggttgagg aagcggctaa gacggctcct     420
ggaaagaaga ggcctgtaga gcagtctcct caggaaccgg actcctccgc gggtattggc      480
aaatcgggtg cacagcccgc taaaaagaga ctcaatttcg gtcagactgg cgacacagag     540
tcagtcccag accctcaacc aatcggagaa cctccccgcag ccccctcagg tgtgggatct    600
cttacaatgg cttcaggtgg tggcgcacca gtggcagaca taacgaagg tgccgatgga      660 gtgggtagtt cctcgggaaa ttggcattgc gattcccaat ggctggggga cagagtcatc      720
accaccagca cccgaacctg ggccctgccc acctacaaca tcacctcta caagcaaatc      780 tccaacagca catctggagg atcttcaaat gacaacgcct acttcggcta cagcaccccc      840
tgggggtatt ttgacttcaa cagattccac tgccacttct caccacgtga ctggcagcga      900
ctcatcaaca caactgggg attccggcct aagcgactca acttcaagct cttcaacatt      960
caggtcaaag aggttacgga caacaatgga gtcaagacca tcgccaataa ccttaccagc      1020
acggtccagg tcttcacgga ctcagactat cagctcccgt acgtgctcgg gtcggctcac     1080
gagggctgcc tcccgccgtt cccagcggac gttttcatga ttcctcagta cgggtatctg     1140
acgcttaatg atggaagcca ggccgtgggt cgttcgtcct tttactgcct ggaatatttc     1200
ccgtcgcaaa tgctaagaac gggtaacaac ttccagttca gctacgagtt tgagaacgta    1260
cctttccata gcagctacgc tcacagccaa agcctggacc gactaatgaa tccactcatc     1320
gaccaatact tgtactatct ctcaaagact attaacggtt ctggacagaa tcaacaaacg    1380
ctaaaattca gtgtggccgg acccagcaac atggctgtcc agggaagaaa ctacataccct   1440 ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct     1620 ttaattttg gcaaacaagg aactggaaga dacaacgtgg atgcggacaa agtcatgata     1680
accaacgaag aagaaattaa aactactaac ccggtagcaa cggagtccta tggacaagtg     1740
gccacaaacc accagagtgc caagcacag gcgcagaccg gctgggttca aaaccaagga    1800
atacttccgg gtatggttgt gcaggacaga gatgtgtacc tgcaaggacc catttgggcc     1860
aaaattcctc acacggacgg caactttcac ccttctccgc tgatgggagg gtttggaatg    1920
aagcacccgc ctcctcagat cctcatcaaa aacacacctg tacctgcgga tcctccaacg   1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac ccgcccat tggcaccaga tacctgactc gtaatctgta a             2211
```